(12) United States Patent
Osorio et al.

(10) Patent No.: US 7,204,833 B1
(45) Date of Patent: Apr. 17, 2007

(54) MULTI-MODAL SYSTEM FOR DETECTION AND CONTROL OF CHANGES IN BRAIN STATE

(75) Inventors: Ivan Osorio, Leawood, KS (US); Naresh C. Bhavaraju, Mission, KS (US)

(73) Assignee: Flint Hills Scientific LLC, Lawrence, KS (US)

( * ) Notice: Subject to any disclaimer, the term of this patent is extended or adjusted under 35 U.S.C. 154(b) by 198 days.

(21) Appl. No.: 10/909,488

(22) Filed: Aug. 2, 2004

Related U.S. Application Data

(63) Continuation-in-part of application No. 10/683,647, filed on Oct. 10, 2003, now Pat. No. 6,793,670.

(60) Provisional application No. 60/418,154, filed on Oct. 11, 2002.

(51) Int. Cl.
  *A61B 18/02* (2006.01)
(52) U.S. Cl. ............... 606/22; 606/21; 607/105
(58) Field of Classification Search .......... 604/95, 604/113; 606/20–26; 607/104–106, 113–114
See application file for complete search history.

(56) References Cited

U.S. PATENT DOCUMENTS

| | | | |
|---|---|---|---|
| 6,190,378 B1 | 2/2001 | Jarvinen | |
| 6,248,126 B1 | 6/2001 | Lesser et al. | |
| 6,549,804 B1 | 4/2003 | Osorio et al. | |
| 6,560,486 B1 | 5/2003 | Osorio et al. | |
| 6,567,696 B2 * | 5/2003 | Voznesensky et al. | 607/3 |
| 6,706,037 B2 * | 3/2004 | Zvuloni et al. | 606/21 |
| 6,726,709 B1 * | 4/2004 | Lennox | 607/105 |
| 7,014,624 B2 * | 3/2006 | Meythaler et al. | 604/113 |
| 2003/0135199 A1 * | 7/2003 | Rosenman et al. | 604/528 |

* cited by examiner

*Primary Examiner*—Roy D. Gibson
(74) *Attorney, Agent, or Firm*—Donald R. Schoonover

(57) ABSTRACT

A multi-purpose device mechanism for sensing and control of changes in brain state includes a shaft portion and extendible elements structured for insertion into target tissue of the brain of a subject patient, cooling means configured to operatively apply cooling therapy to the target tissue, stimulation means having at least one electrical contact structured to operatively apply electrical stimulation therapy to the target tissue, sensing means including at least one sensor monitoring a biological signal of the subject patient, control means responsive to the sensing means wherein the control means is structured to, in response to signals from the sensing means that indicate the presence of a predetermined physiological condition or occurrence of an undesirable state change, automatically cause the cooling means and/or the stimulation means to initiate or terminate the cooling therapy and/or the electrical stimulation therapy respectively and an energy source for powering the various components of the multi-purpose device mechanism. A modified embodiment includes a least one spiral conduit and at least one return conduit for cycling coolant or refrigerant to and from the shaft portion and an external reservoir. Another modified embodiment includes pressurizing means for extending at least one extendable tube into brain tissue surrounding the shaft portion.

12 Claims, 12 Drawing Sheets

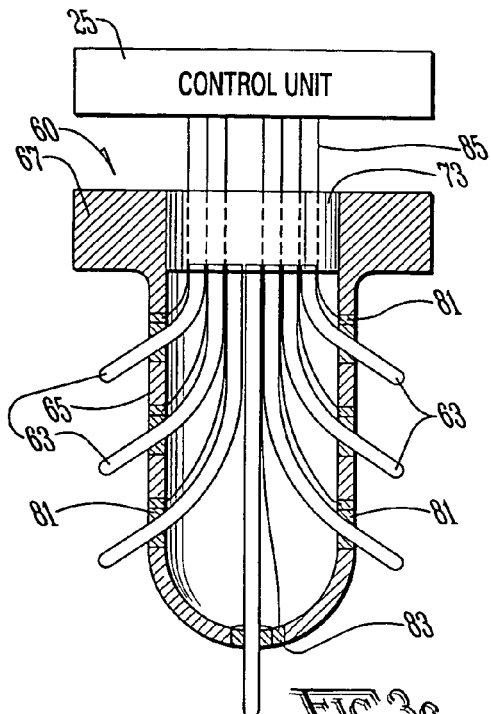
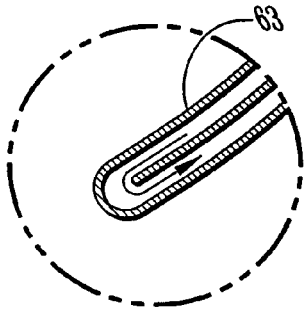
Fig.3c
Fig.3d
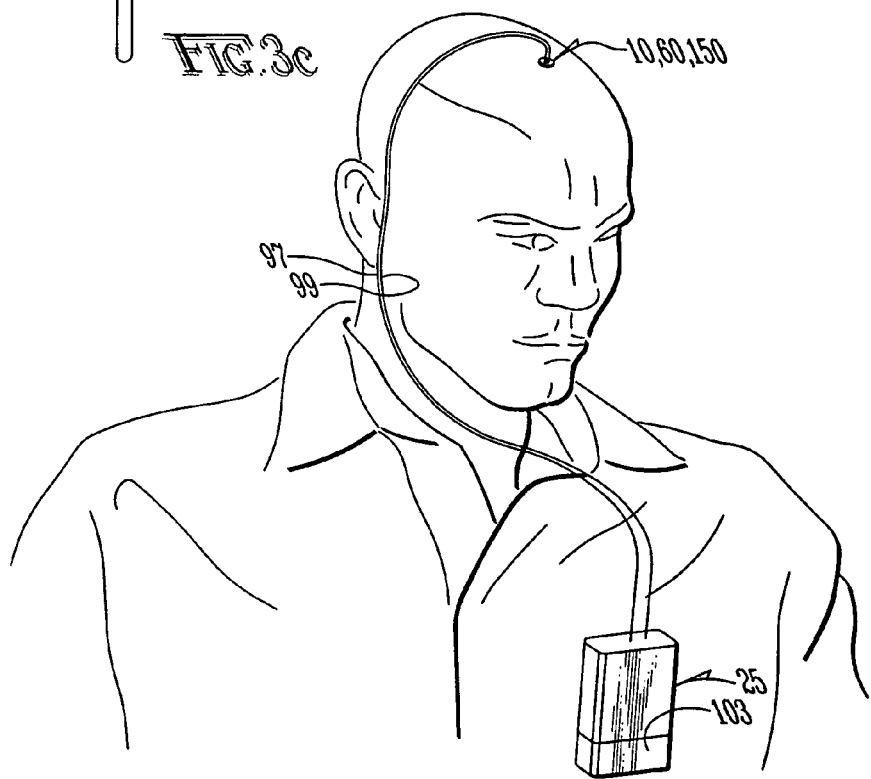
Fig.4a

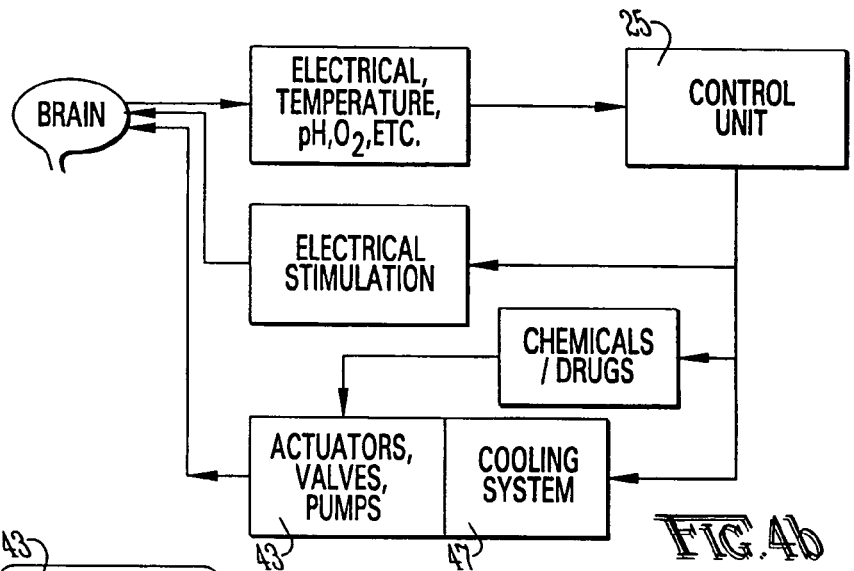
FIG.4b
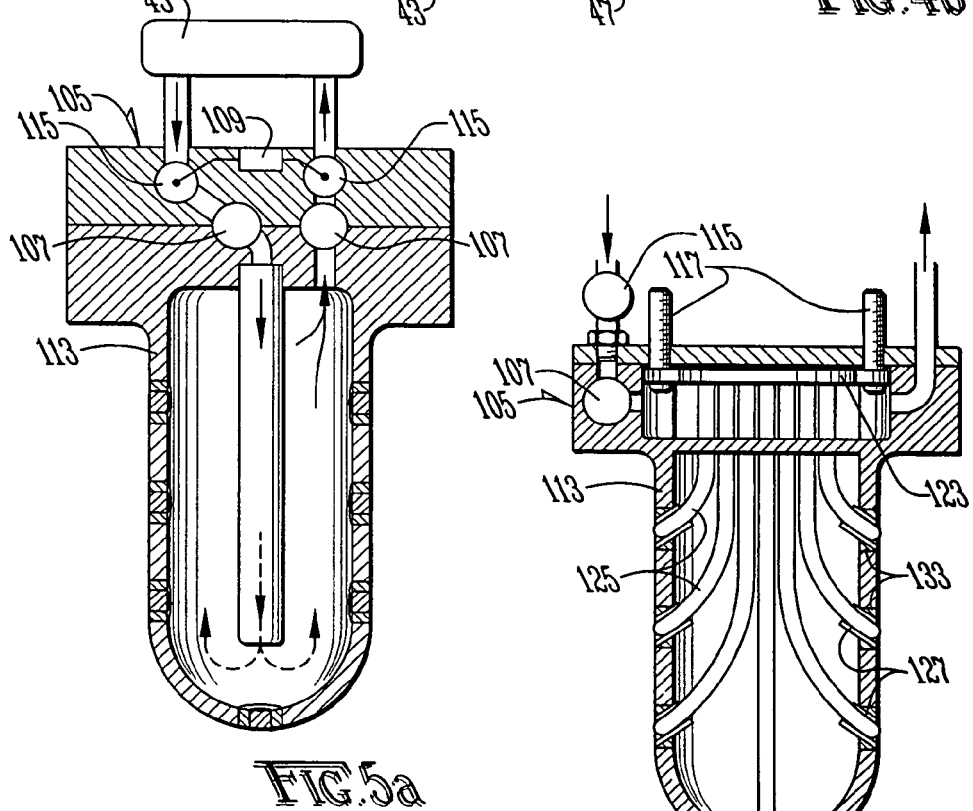
FIG.5a
FIG.5b

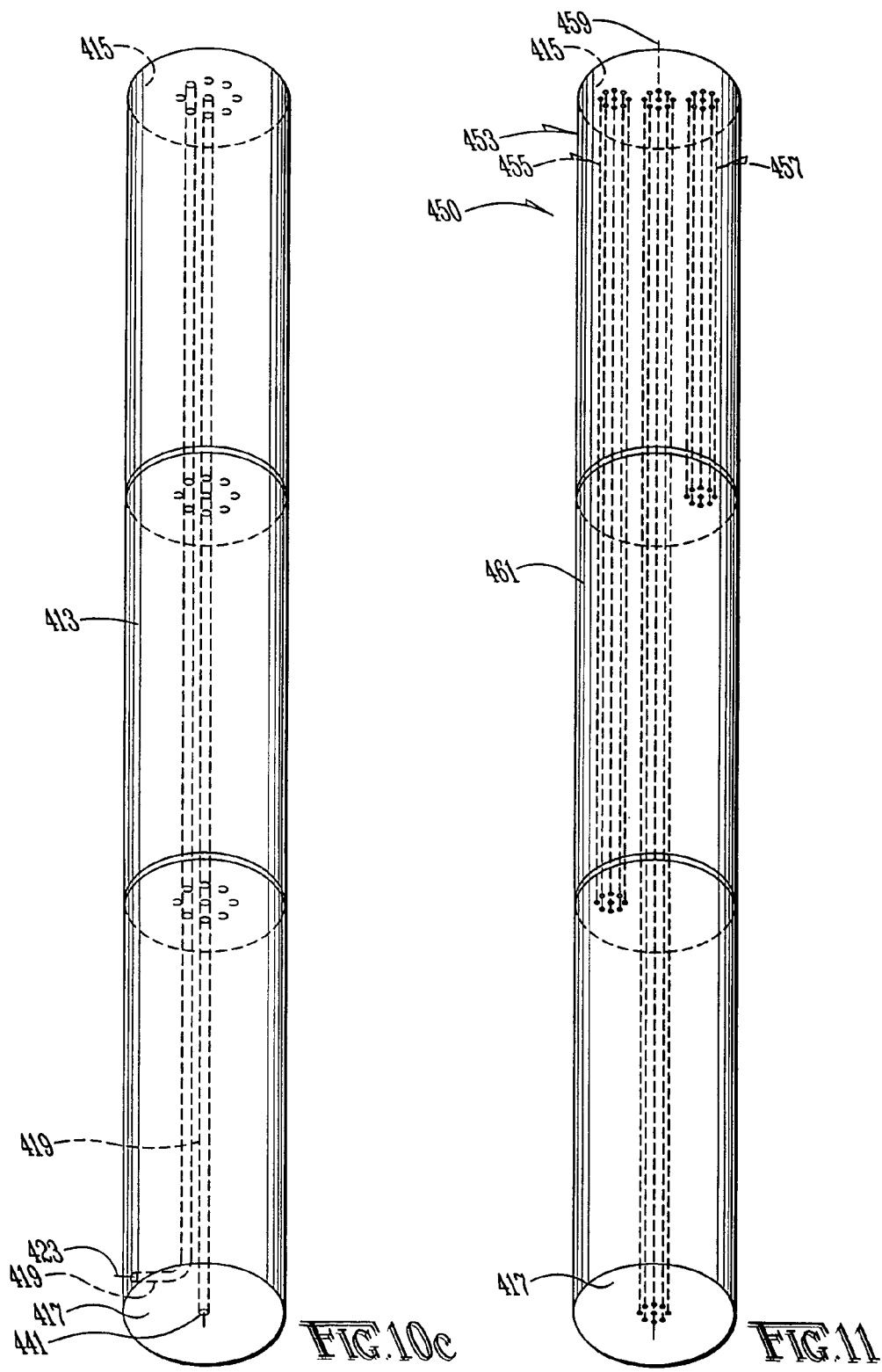

MULTI-MODAL SYSTEM FOR DETECTION AND CONTROL OF CHANGES IN BRAIN STATE

CROSS REFERENCE TO RELATED APPLICATIONS

This application is a continuation-in-part of patent application Ser. No. 10/683,647 filed Oct. 10, 2003 and entitled, "Multi-modal System for Detection and Control of Changes in Brain State," now U.S. Pat. No. 6,793,670, which is based on Provisional Patent Application Ser. No. 60/418,154 of Ivan Osorio et al, filed Oct. 11, 2002 and entitled "Multi-modal System for Detection and Control of Changes in Brain State."

BACKGROUND OF THE INVENTION

1. Field of the Invention

The present invention is related to medical treatments involving the human brain and, more specifically without limitation, to real-time automated sensing and contingent, or closed-loop prevention/control or blockage of brain state changes using at least electrical or thermal signals either individually or simultaneously for detection or prediction of seizures or sensing of other changes in brain states; automated timely and safe delivery of cryogenic or other therapies; quantitative assessment of their efficacy and safety; and means for optimization thereof.

2. Discussion of the Related Art

Neuronal and, by extension, brain metabolic and electrical activity of poikilothermic and homeothermic animals are without exception temperature-dependent. Low temperatures (below 35° C.) in homeotherms, and more specifically in humans, have an easily discernible effect on behavior and on an EEG, which is a reliable index of cortical electrical activity. At such temperatures, cerebral blood flow, oxygen and glucose consumption become depressed and, due to tight electro-metabolic coupling, so does neuronal function and its by-product, electrical activity. Brain cooling has a protective effect on the integrity of its tissue, a feature that has its own therapeutic applications.

For example, hypothermia minimizes damage in models of brain ischemia by decreasing both the metabolic demand of the brain tissue and the production of glutamate and dopamine, which under certain conditions can be excitotoxic. These effects make hypothermia well-suited for the treatment of neurological diseases that are characterized by the following:

1) absolute or relative, global or local neuronal hyper excitability, such as in epilepsy;
2) an imbalance in the degree of neuronal activity between/among structures which form part of a functional network, such as in Parkinson's disease;
3) reduction in the supply of energy substrates, such as in stroke; and
4) activation/release of pathoclitic enzymes, such as in trauma, stroke, infection or prolonged/frequent seizures (status epilepticus).

Cooling can also be used for functional cortical localization or assessment of cognitive functions to assist in neurosurgical planning. Cryogenics has definite important advantages over electrical stimulation, the current standard for cortical localization, as follows:

a) cooling, unlike electrical stimulation (ES), does not precipitate seizures; and b) unlike ES, which requires at least two stimulating electrodes and which has the potential to reach all structures between the electrodes and even those remote to them via existing neural pathways, the effects of cooling remain more localized and are more gradual than ES, thus providing more selective and interpretable information and also a higher therapeutic index.

Although cooling of brain tissue has been an object of several prior art approaches for various medical treatments, most of those approaches have been limited to cooling the most superficial layers of small cortical areas or in some cases just the scalp. Some other prior art approaches utilize cryogenic energy to ablate or destroy brain tissue. Cooling for the sole purpose of tissue ablation/destruction requires processing of very few, if any, input signals and parameter controls whereas reversible safe cooling of brain tissue for control of state changes such as seizure blockage, as taught by the present disclosure for seizure blockage purposes, is a highly time-sensitive task. For example, while methods for measuring tissue properties, such as thermal conductivity for the purpose of controlling the extent and degree of freezing, which is an irreversible destructive procedure, are disclosed in U.S. Pat. No. 6,190,378, that procedure is neither time-sensitive nor dependent on the sensing of changes in electrical or thermal signals as required for seizure blockage using reversible cooling. No prior art reference appears to disclose seizure blockage as taught herein; references that border on such an application appear to have very limited usefulness or relevance for the medical applications disclosed herein. One prior art reference discloses means to block seizures through reversible cooling, namely U.S. Pat. No. 6,248,126 to Lesser et al, but has significant limitations, which make it highly unlikely that seizures can be blocked using such a device, even if the seizures originate from exposed gyri, designated by numeral 4 in FIG. 1, for the following reasons:

1) placement of the device of the '126 patent over the most superficial cortical layer of exposed gyri as taught by the '126 patent prevents timely cooling of deeper cortical layers (IV-VI) from where most seizures originate because (a) there are no means for attachment and, as a result, the cooling device floats over the cerebrospinal fluid and the fluid currents, through convection, carry cooling energy away from the target site thereby slowing down the rate at which tissue cooling can occur at the most superficial cortical layers; and (b) thermal diffusivity of brain tissue is such that rapid or timely cooling of deeper layers to block seizures can not take place; and 2) the majority of cortical gyri are not exposed, designated by numeral 5 in FIG. 1, and thus are not amenable to cooling using such a device.

Epilepsy affects about 2.7 million people in the United States and about 60 million worldwide. Approximately 30% of this population has pharmaco-resistant epilepsy, defined as at least one monthly seizure despite treatment with appropriate drugs at therapeutic concentrations. New therapies, which are both safe and effective, are required, given the existent, unmet need. Cooling of brain tissue is one such therapy with great potential as its effects are fully reversible and safe since the range of effective temperatures has no adverse effects on tissue viability or integrity and it is not known to precipitate or worsen seizures. While as early as 1974, it was shown that lowering the temperature of the midbrain prevents epileptiform activity, this therapeutic modality has received little attention due mainly to lack of suitable implantable devices and of interest in therapies other than pharmacological ones. Newly published evidence lends more support for an anti-seizure role for cooling of brain tissue. For example, U.S. Pat. No. 6,248,126 to Lesser et al discloses the use of a device based on the Peltier effect for cooling small areas of the cortical surface for seizure control. That device has important practical limitations, as described below, which translate into reduced efficacy and applicability. For example, that device does not provide a means to transfer heat (or cooling) in a timely manner from the surface to deeper neocortical regions from where seizures originate, which considerably limits efficacy since the delay in delivering therapy to critical regions allows the seizure to spread and gain intensity. This delay is explained by the fact that temperature gradients are steep and limit cooling to the immediate vicinity of the device, which necessitates that the cooling source be located as close to the target as possible for the therapy to be effective. Thermal diffusivity brain models reveal that lowering the temperature of a region located 5 mm from the cooling source, which is the average width of the cortex, from 37° C. to 16° C. takes approximately thirty seconds. Since placement of a Peltier device as taught by Lesser et al is on the cortical surface and the distance between that Peltier device and the seizure-generating cortical layers is about 5 mm, it is highly unlikely that they can be cooled down sufficiently timely to block seizures and prevent their spread. For any contingent therapy to be efficacious, it must reach the site of origin within five seconds of seizure onset. The ability to rapidly reach the seizure-generating tissue tissue-generating seizures (epileptogenic region) is essential for the success of cryogenic therapy. Moreover, the device and approach of the '126 patent do not have the means to monitor tissue electrical activity required to maximize efficacy, minimize the risk of freezing the tissue, assess therapeutic efficacy, and operate efficiently. Other prior art cooling catheters and probes are not suitable for use in epilepsy.

Cooling offers certain advantages over electrical stimulation for control of state changes or of cortical or subcortical functions as follows:

a) the only critical control parameter in cooling therapy is temperature as compared to intensity, frequency, pulse width, waveform, size and orientation of the field which determine efficacy and safety of electrical stimulation;

b) cooling has a greater safety margin than electrical stimulation because of the less instantaneous nature of the change in temperature particularly at the device-tissue interface, as opposed to charge deposition over the area covered by the electrical field and the known ability of electrical stimulation to induce seizures when certain parameters are utilized; and c) cooling allows good-quality recording of electrical brain signals during cryogenic therapy for continuous real-time assessment of efficacy, an important function which can not be accomplished during delivery of electrical therapy, since electrical therapy saturates amplifiers and distorts brain electrical activity, not only for the duration of the electrical stimulation but also for a few seconds after its conclusion, which precludes meaningful analysis and valid interpretation of brain electrical signals during a certain period. However, since electrical diffusivity is much higher than thermal diffusivity, electrical therapy may have quicker effects than is realizable from cryogenic therapy.

One of the therapies used for epilepsy and other neurological disorders is drugs. Any brain-acting drug given orally or intravenously must be able to cross the blood-brain barrier. The blood brain barrier (BBB) only allows certain small lipid soluble compounds through, thus protecting the brain against certain toxic substances which circulate in the blood stream. While this is a life supporting protection for the brain, the existence of the BBB limits the amount and rate of delivery of most drugs. Direct drug or chemical delivery to brain targets (thereby bypassing the BBB) has certain advantages over the systemic and intravenous route. Direct drug delivery into brain may be achieved via conduits (macro-, micro- or nano-tubes), nanoparticles, drug carrying polymers, and drug delivery matrices. However, the chemical (mass transfer) diffusivity of the brain is low, which makes it difficult for the drugs to diffuse throughout the brain. For this reason, the drug to be used must be placed as close to the target of interest as possible and depending on the application, its diffusion rate may be enhanced using physical (i.e., ultrasound) or chemical means. The natural limitations to brain drug diffusion, are partially overcome by the current invention, which makes it possible to reach the deeper layers of the cortex and enables drugs to be delivered closer to target regions/structures, than prior art.

What is needed is a multi-purpose device, which the present invention provides for single, dual, simultaneous or sequential electrical and/or cryogenic and/or pharmacologic therapy for control of brain state changes or of cortical and subcortical functions. What is also needed is a cooling or other therapeutic device that is principally, but not only, activated in response to a cue including, but not limited to, sensing of a seizure, to thereby minimize power consumption, a prerequisite for miniaturization and implantation.

SUMMARY OF THE INVENTION

The improvement of the multi-purpose device mechanism of the present invention for sensing and control of changes in brain state includes a shaft portion structured for insertion into target tissue of the brain of a subject patient, cooling means configured to operatively apply cooling therapy to the target tissue, sensing means including at least one sensor monitoring a biological signal of the subject patient, control means responsive to the sensing means wherein the control means is structured to, in response to signals from the sensing means that indicate the occurrence of a change of state, automatically cause the cooling, electrical or pharmacologic means to initiate or terminate the cooling therapy, and an energy source for powering the various components of the multi-purpose device mechanism.

The cooling, electrical or pharmacologic means of the multi-purpose device mechanism includes at least one extendable element housed within the shaft portion and structured to be extended outwardly from the shaft portion into target tissue, either manually or by motor means. The at least one extendable element for cryogenic therapy includes at least one cooling element, which may be hollow with a closed distal end and a dividing wall that extends from near the proximal end to near the distal end thereof that separates the at least one cooling element into side-by-side first and second channels with fluid flow communication between the first and second channels at the distal end thereof, or may be constructed of a solid material having high thermal conductivity. The cooling means also includes either a reservoir for containing coolant and pumping means structured to pump coolant to and from the reservoir and to the at least one cooling element, or a refrigerant source containing refrigerant at an elevated pressure, distribution means for distributing the refrigerant from the refrigerant source to the at least one cooling element, and means for removing the refrigerant from the cooling element or from the shaft portion.

Intraparenchymal use of cooling probes increases temporo-spatial resolution but it imposes limits on their size (to decrease the risk of neurological complications), especially their diameter and thus their cooling capacity, since they can accommodate lower volumes of coolant or refrigerant compared to larger probes. Also, the smaller the probe the more cumbersome and costly its manufacturing and the greater the pressure required to circulate the coolant inside/through it. One approach that will enable the intraparenchymal use of larger size probes without considerably increasing the risk or seriousness of neurological complications and without degradation in performance, consists of placing at least one probe into a cerebral ventricle and once inside it, deploying the extendible elements (if required for the application) through the ventricular lining into the target structures. Several possible embodiments may be considered:

1. To minimize loss of thermal energy through convection, the portions or areas of the shaft in direct contact with the cerebro-spinal fluid may be insulated and those abutting the cooling target may be non-insulated to allow more selective transfer of thermal energy. Cooling probes such as those depicted in FIG. 3 may be used for this application with appropriate modifications.

2. A probe with extendible elements deployed into the cooling target may be insulated over the entire surface of the shaft to maximize cooling of said extendible. Signals may be acquired from brain tissue, CSF or both through these probes and/or their extendible elements. The following is provided only as an example and is not intended to limit the scope of the applications: electrodeA device (FIG. 12) may be placed in the temporal horn and the extendible elements may be deployed on the mesial side of the shaft into the hippocampus to cool it and record the signals from it. The shaft portion of the probe may also be used to cool the fluid in this or other ventricles as required by the application. As already disclosed earlier, the shaft of the intraventricular probe may be used to keep the tissue (i.e., hippocampus) temperature below normal continuously or during periods of high seizure likelihood (pre-cooling mode) but above that which it would negatively affect baseline function. The purpose of pre-cooling tissue is to increase the speed of cooling of the target structure to block an undesirable or abnormal state change (i.e. seizures) in response to sensing of said state change. Increase in the rate of cooling may be also achieved by: a) using two separate devices, one placed inside the ventricle and the other placed directly into the cooling target (i.e., hippocampus) and b) using a single device whose the shaft placed inside the ventricle is used for pre-cooling and whose extendible elements inserted into the hippocampus, are used for cooling the target in response to sensing of a state change.

The sensing means may include a sensor or sensors positioned in one or more of the extendable elements and may include one or more sensors mounted on the shaft portion to operatively contact target tissue adjacent thereto.

The multi-purpose device mechanism may also include stimulation means having at least one electrical contact structured to operatively apply electrical stimulation therapy to the target tissue wherein the control means, in response to signals from the sensing means that indicate the occurrence or presence of a change of state, is structured to automatically cause the stimulation means to initiate or terminate the electrical stimulation therapy. Devices for electrical stimulation capabilities may also be placed inside a ventricle. For this application the shaft inside the ventricle will be electrically insulated and only the extendible elements will conduct electricity.

The cooling means of multi-purpose device mechanism may include at least one thermoelectric device. The multi-purpose device mechanisms may also include means for delivering chemical therapy to the target tissue.

The sensing means and control means of the multi-purpose device mechanism may be structured to sense and control one-, two-, and/or three-dimensional configurations. The sensing means may be structured to sense chemical signals arising from ions, neurotransmitters and/or pH, and/or to sense physical signals such as infrared, pressure and/or acoustics.

A modified embodiment of the multi-purpose device mechanism for sensing and control of changes in brain state includes a shaft portion structured for insertion into target tissue of the brain of a subject patient; cooling means configured to operatively apply cooling therapy to the target tissue, wherein the cooling means includes a least one spiral conduit structured to carry coolant or refrigerant from an external reservoir to and through the shaft portion; and at least one return conduit structured to provide a return path to the external reservoir for the coolant or refrigerant carried by the at least one spiral conduit; sensing means including at least one sensor monitoring a biological signal of the subject patient; control means responsive to the sensing means wherein the control means is structured to, in response to signals from the sensing means that indicate the occurrence of a change of state, automatically cause the cooling means to initiate or terminate the cooling therapy; and an energy source for powering the various components of the multi-purpose device mechanism. The at least one return conduit of the cooling means includes a return conduit centrally located within the at least one spiral conduit. A variation of the modified embodiment includes the at least one spiral conduit of the cooling means having two spiral conduits intertwined in a double helix configuration, and the at least one return conduit of the cooling means having one return conduit centrally located within the two spiral conduits to provide a return path to the external reservoir for the coolant or refrigerant carried by the two spiral conduits. A further variation includes the at least one spiral conduit of the cooling means having two spiral conduits with a double helix configuration, and the at least one return conduit of the cooling means having two separate return conduits positioned within the two spiral conduits to provide separate return paths to the external reservoir for the coolant or refrigerant carried by the two spiral conduits.

Another modified embodiment of the present invention includes a shaft portion structured for insertion into target tissue of the brain of a subject patient; cooling means configured to operatively apply cooling therapy to the target tissue, wherein the cooling means has at least one extendable tube housed within the shaft portion and structured to be extended outwardly from the shaft portion, and pressurizing means structured to sufficiently pressurize the at least one extendable tube to thereby advance the at least one extendable tube into brain tissue surrounding the shaft portion; sensing means including at least one sensor monitoring a biological signal of the subject patient; control means responsive to the sensing means wherein the control means is structured to, in response to signals from the sensing means that indicate the occurrence of a change of state, automatically cause the cooling means to initiate or terminate the cooling therapy; and an energy source for powering the various components of the multi-purpose device mechanism. The pressurizing means is structured to sufficiently pressurize the at least one extendable tube to enhance the rigidity of the at least one extendable tube to thereby overcome elasticity of the brain tissue surrounding the shaft portion. The distal end of the at least one extendable tube is structured to facilitate insertion of the at least one extendable tube into the brain tissue surrounding the shaft portion, such as by tapering into a sharp point or edge.

Another embodiment of the invention includes the use of a combination of different modalities for improving the efficacy of therapy. For example, drug delivery, temperature regulation and electrical stimulation can all be used simultaneously or in some other relation in time to achieve or block brain state changes.

In all the embodiments of the devices disclosed above, the device shaft, the base or the extendible elements may be used as a reference for stereotaxy. Fiduciary markers may be placed on selected locations on the device so that they are visible to x-ray, MRI or any such scans. For this purpose, the device may be coated with a thin layer of photo-opaque radio-opaque dye. The fiduciary markers may be aimed at the intended stereotaxic target to increase precision and facilitate verification of placement. These fiduciary markers may be used to aid in the localization of other targets or in the placement of additional devices.

PRINCIPAL OBJECTS AND ADVANTAGES OF THE INVENTION

The principal objects and advantages of the present invention include: providing a multi-purpose device that can be used to detect relevant one-, two-, or three-dimensional changes in electrical, chemical or thermal or other types of signals reflective of brain state; providing such a multi-purpose device that can be used to control or prevent changes in brain state by, for example, lowering, in real-time, brain temperature at the cortex, white matter, subcortical structures or cerebro-spinal fluid for one-, two-, or three-dimensional detection or treatment purposes; providing such a multi-purpose device that can be used to evaluate the efficacy of therapy in real time while the therapy is being delivered and optimize it; providing such a multi-purpose device that can provide electrical, chemical or thermal, or other feedback to a control system connected to the device; providing such a multi-purpose device that can be used to evaluate the safety of therapy in real time while the therapy is being delivered to thereby minimize the risk of injury to tissue being treated; providing such a multi-purpose device that can be used to detect and control, in a timely fashion, undesirable or pathological changes in brain, spinal cord, spinal roots, or peripheral nerves of states such as stroke, trauma, depression, pain movement disorders, cognitive functions, behavior or emotions or physiological ones, such as changes in level of attention, drowsiness, and others; providing such a multi-purpose device that may be used to effect cooling of brain tissue in response to changes in signals other than electrical or thermal, which may occur prior to or at the onset of changes in brain state, such as signals arising from cardiovascular, autonomic, chemical (pH, $[Ca^{++}]$, $[K^+]$, amino acids, energy substrates, catabolic products, free radicals, etc.) or physical (pressure, sound, optical, etc.) phenomena; providing such a multi-purpose device that has hollow spiral coolant- or refrigerant-carrying tubes that enable enhanced cooling of target brain tissue; providing such a multi-purpose device that includes pressurizing means for extending an extendable tube or tubes into surrounding brain tissue; and generally providing such a multi-purpose device that is reliable in performance, capable of long lasting life, and particularly well-adapted for the proposed usages thereof.

Other objects and advantages of this invention will become apparent from the following description taken in conjunction with the accompanying drawings wherein are set forth, by way of ill

BRIEF DESCRIPTION OF THE DRAWING FIGURES

FIG. 2b is a schematic representation of the multi-purpose device for sensing and control, through cooling, of changes in brain state depicted in FIG. 2a.

FIG. 3c is yet another depiction of the modified embodiment of the multi-purpose device for sensing and control of changes in brain state similar to FIG. 3b but also showing a sensor thereof.

FIG. 3d shows a magnified view of the tip of the extendible element circled in FIG. 3a.

FIG. 4a is a schematic representation of the multi-purpose device for sensing and control of changes in brain state connected to a subject patient.

FIG. 4b is a schematic representation of various components of the multi-purpose device for sensing and control of changes in brain state connected to the brain of a subject patent.

FIGS. 5a and 5b depict various components of the multi-purpose device for sensing and control of changes in brain state for effecting the flow of coolant or refrigerant therethrough.

FIG. 10C illustrates a conduit or tube structured and configured to direct a wire or contact extending therethrough in a particular direction.

FIG. 11 depicts a variation of the device shown in FIG. 10A, wherein the clusters of hollow conduits or tubes are arranged in both concentric and non-concentric patterns, according to the present invention.

DETAILED DESCRIPTION OF THE PREFERRED EMBODIMENTS

Figure 1:
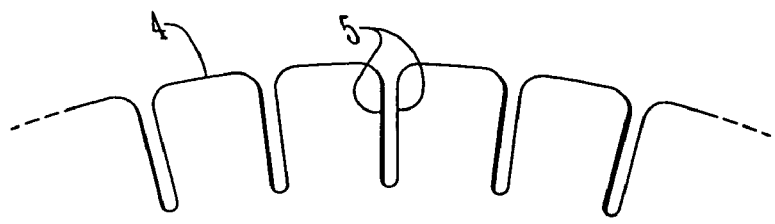
FIG. 1 is a depiction of the cortex, showing both exposed and unexposed portions.

As required, embodiments of the present invention are disclosed herein, however, it is to be understood that the disclosed embodiments are merely exemplary of the invention, which may be embodied in various forms. Therefore, specific structural and functional details disclosed herein are not to be interpreted as limiting, but merely as a basis for claims and as a representative basis for teaching one skilled in the art to variously employ the present invention in virtually any appropriately detailed structure.

The present invention disclosed herein overcomes the limitations of prior art approaches for sensing and control of changes in brain state by: a) monitoring and processing brain physical (i.e. electrical and/or thermal) and/or chemical signals in real-time for the prediction and detection of seizures or of sensing undesirable brain state changes; b) utilizing feedback controls and means for timely delivery, and cessation of delivery, of cryogenic and/or electrical and/or chemical control means to the area or structures r circuits mediating the undesirable changes (i.e. seizures) to optimize device performance, and for therapeutic efficacy and safety in an individualized manner. The present invention substantially improves state-of-the-art approaches by providing:

1) automated means for cooling brain tissue in a temporally selective manner, i.e., in response to seizure detections or to neuronal behavior or conditions associated with a high likelihood of seizure occurrence or of other changes in brain states, using the brain's electrical activity or temperature input signals;

2) means for cooling brain tissue in a spatially selective manner to thereby decrease undesirable side effects and power consumption by the device and to increase therapeutic efficiency by limiting delivery of cooling therapy to only a target site of interest;

3) automated feedback to and from a cooling device for regulating and keeping the temperature of cooling being applied to target tissue within a safe and therapeutic range for the subject patient based on measurements of tissue temperature or electrical activity changes of the brain; and 4) means for measuring real-time therapeutic efficacy and either continuing or terminating the intervention.

5) means for rapid delivery of cooling to epileptogenic tissue or to tissue that mediates changes in brain state. Those skilled in the art would appreciate that electrical and chemical means of preventing or blocking changes of states may complement cooling.

The invention disclosed herein is based on the knowledge that (i) seizures or other changes in brain states are manifested with changes in electrical and chemical/metabolic activity, and (ii) seizures and other changes in brain states are accompanied by changes in local tissue temperature.

Based on the disclosure herein, it will be evident to those familiar with the pertinent art, that the disclosed invention significantly enhances the ease of use, safety and efficacy, of cryogenic therapy over the approaches of the prior art.

The present invention utilizes, in its preferred embodiments, a unitized device which simultaneously allows (i) sensing of changes in brain state using electrical, thermal, chemical, physical, or other types of signals, and (ii) delivery of cryogenic therapy, and simultaneously of electrical stimulation and/or chemical therapy if desired, to all cortical layers including at the top, bottom, and inner wall of exposed and unexposed gyri, and to the white matter and subcortical structures if desired, thereby overcoming the inherent limitations imposed by low thermal diffusivity in brain tissue and minimizing the thermal exchange losses through convection that limit applicability of prior art approaches. Those skilled in the pertinent art will realize from the disclosure herein that other means of delivering cooling to, or exchanging thermal energy with, brain tissue may be used for sensing and control of state changes.

The present invention includes several embodiments that reflect different modes of operation for different applications. Nervous system or brain state changes may be predicted or detected using sensors for changes in temperature, electrical activity, chemical or physical signals that activate delivery of cooling therapy or of electrical stimulation or of chemical therapy, or both, or all by the multi-purpose device of the present invention to the target site or sites of interest. As relevant signals at those sites reach a critical level indicative of state change, the target tissue or region receives cooling therapy in a controlled manner until the detected abnormality is eliminated, or a safety constraint such as a temperature of 4° C. at the device-tissue interface is reached.

In a modified embodiment of the present invention, brain tissue which mediates or generates state changes is pre-cooled and continuously maintained in-between state-changes at a temperature that is lower than normal but is above that which blocks the state transition, to thereby minimize delay in applying therapy. Upon sensing of signal changes indicative of an impending change of state, the device of the present invention is activated so that the tissue or region temperature may be further cooled to a desired therapeutic level. This approach, which speeds up the effects of cooling, may be used in cases wherein the rate of temperature change as a function of tissue volume or area of a target tissue or region is not adequate for control purposes as determined by real-time thermal or electrical or chemical feedback, an aspect not provided by prior art approaches.

Delivery of chemical compounds and electrical stimulation both are known to be useful in controlling certain brain states and/or changes between states. However, their usefulness can be enhanced by relating the time(s) at which they are delivered to the time(s) at which temperature regulation therapy is applied. Multimodal control (cooling+electrical stimulation, cooling+chemical delivery, or cooling+electrical stimulation+chemical delivery) of brain state changes can be exerted through the device disclosed herein; any or all of the control modalities in any combination may delivered in any temporal sequence, including simultaneously, using the same (one) device. The multimodal approach provides a generalization of any prior single-modality therapy, thereby offering improved efficacy, tolerability and safety than unimodal (i.e., electrical stimulation). This may be due in part to a potential synergism among these modalities, so that the decrease in temperature, current densities and amounts of chemicals required to block or abort a change of state, may be lower when delivered in combination than when delivered singly. Delivery of chemical compounds using the devices disclosed herein, will be through openings or perforations in the main shaft and/or extendible elements and will require that the device has as many compartments as there are control modalities. For example, in the case of a device for cooling and delivery of chemical compounds, each will flow through separate compartments hermetically sealed to avoid contamination. The pores or holes in the main shaft or extendible elements may be continuously open or may have a micro- or nano-valves whose opening and closing will be controlled by an actuator mechanism or other mechanism with similar functional capabilities. Control modalities may share extendible elements or may be delivered through separate ones.

FIG. 1 depicts the human cortex. The electrical activity generated in the deeper layers is either not accessible or accessible to devices placed over the most superficial layer of exposed gyri only after a delay from the time the electrical activity is actually generated. This results in either no detection for unexposed gyri or late sensing of state changes, limitations not recognized or taken into account by present state-of-the-art approaches which are greatly compounded by an even larger delay, when attempting to apply cooling therapy to deeper layers when the cooling source is placed over the cortical surface as taught by the prior art.

Basic design criteria of the devices of the present invention are disclosed in U.S. patent application Ser. No. 10/622,238 to Ivan Osorio et al, filed Jul. 18, 2003, which is incorporated herein by reference. Briefly, the devices of the present invention enable simultaneous measurement of brain signals (physical such as thermal or electrical and chemical signals such as neurotransmitters) from exposed and unexposed cortical gyri, both from their depths and from their surfaces, white matter or subcortical nuclei, thereby providing precise localization and delivery of therapy or other means of control to any of those locations without appreciable delay and with precision otherwise not previously attainable. By simply increasing the length of the devices of the present invention, the recording or sensing and control range of the devices and system may be considerably increased. In other words, signals may be recorded simultaneously and controlled, without considerable delay and with great precision, from the surface and depths of the cortex, from the white matter, and from radially aligned subcortical structures such as the thalamus, using the same device.

Figure 2A:
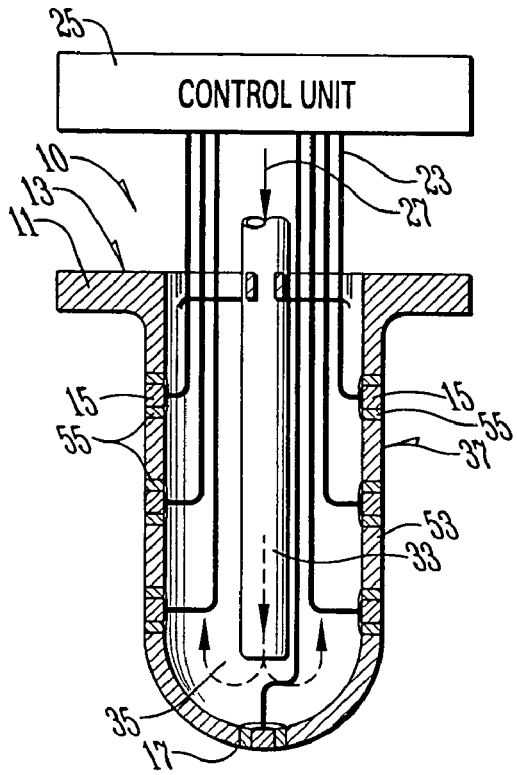
FIG. 2a depicts a multi-purpose device for sensing and control of changes in brain state, according to the present invention.
Figure 2B:
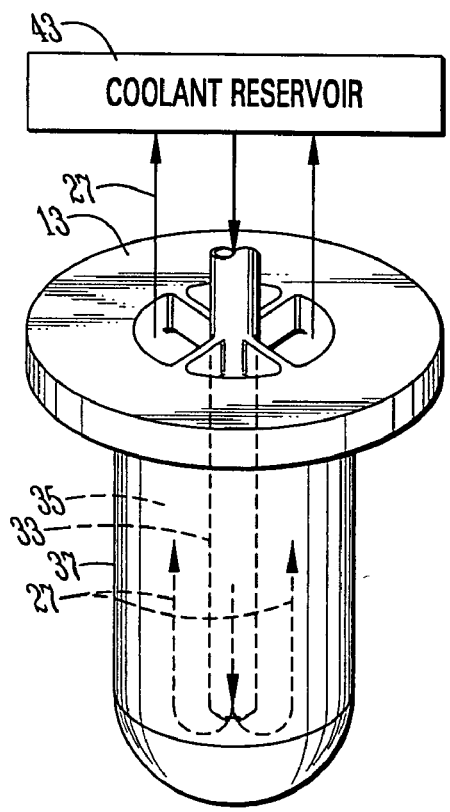

FIG. 2a depicts an embodiment of the present invention 10 that comprises device structure 13 with at least one sensor 15 for acquiring physical (i.e., electrical, thermal), chemical (i.e., ion concentration, oxygen, neurotransmitters) or other types of physiological biological signals, and at least one cooling surface 17. Temperature sensing and monitoring may be achieved with small thermocouples, thermistors, surface acoustic wave technology or other suitable miniature or micro temperature sensors. For other monitoring or recording signals, such as those arising from pH, $O_2$ saturation, neurotransmitters, etc., various miniature or micro sensors are presently available for such purposes. When configured to record electrical activity, sensor 15 may also be used for injecting current into, or for applying electrical stimulation therapy to, brain tissue. Contacts or sensors 15 used for recording or monitoring purposes are connected to conductors 23 that carry signals to and from the sensors 15 to control apparatus 25 situated outside the device 13. Fluid 27, such as saline cooled to an appropriate temperature, flows through an inner tube 33 to an outer cavity 35 defined by shaft 37 and back into a coolant reservoir 43, as schematically depicted in FIG. 2b. Although various coolants may be used, sterile saline with preservatives or antimicrobials is preferred due to its biological safety and high thermal capacity.

The circulation of coolant 27 through the tube 33 and cavity 35 is controlled by units, depicted in FIGS. 4 and 5 and as hereinafter described, which operate based on inputs from sensors 15. Control units 25, see FIGS. 4a and 4b, may include a microprocessor in addition to analog or digital apparatus and are connected to a coolant circulating system 43 that may include devices 47, such as actuators, valves and/or pumps, to control the flow of coolant or refrigerant through the device 10. Sensing of state change using any of the signals described herein, and as disclosed in U.S. Pat. No. 6,549,804 to Ivan Osorio et al, issued Apr. 15, 2003 which is incorporated herein by reference, enables circulation of coolant 27 through the device 10, which circulation can be terminated based on a pre-determined threshold of sensor signals for efficacy or safety. The shaft 37 also includes insulating portions 53 for separating cooling surfaces 17, sensors and electrical contacts 15 from each other. The insulating portions 53 are constructed of materials such as polyurethane, Teflon or other suitable materials, such as Tecoflex™ or Silastic™ for example, that preserve the flexibility of the shaft 37. Those skilled in the art can appreciate that the location and extent of the insulating portions 53 and of the cooling surfaces 17 can be varied according to any particular application or the shape of the device. Coolants 27 or refrigerants are prevented from leaking into the surrounding brain tissue by using medical, biocompatible seals 55, such as those presently available for such purposes. The mechanisms for transferring coolant or for cooling may include micro-fluidic pumps, miniature heat pumps, miniature heat absorption systems, thermoelectric coolers, miniature evaporation systems working with cryogenic fluids or other presently available pumps, which can facilitate fluid flow through micro-channels, such as the tubes inside the devices described herein. Those skilled in the art can appreciate that signal transmission between sensors 15 and control unit 25 may be wireless. In that event, the device 10 would include a miniaturized transmitter mounted in the base 11. The base 11 may also be used for cooling the surface of the brain.

Figure 3A:
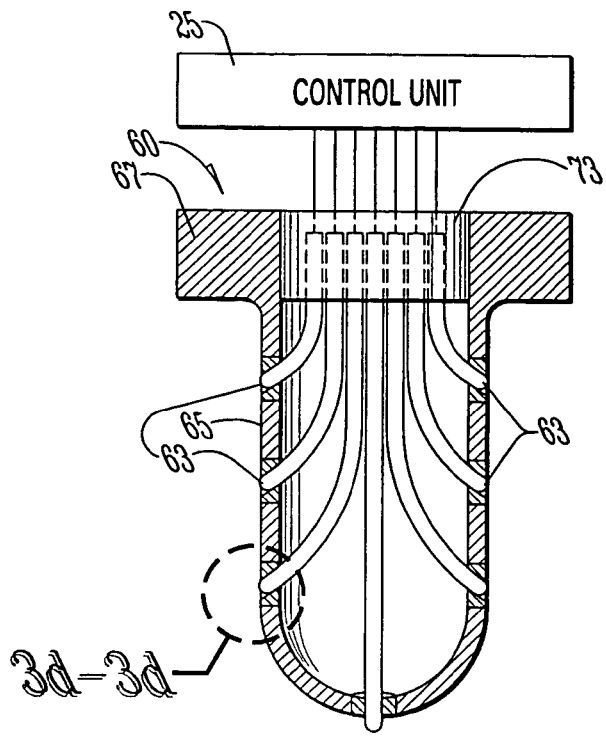
FIG. 3a is a depiction of a modified embodiment of the multi-purpose device for sensing and control of changes in brain state having extendable elements housed in a shaft portion wherein the elements are shown in a retracted configuration.
Figure 3B:
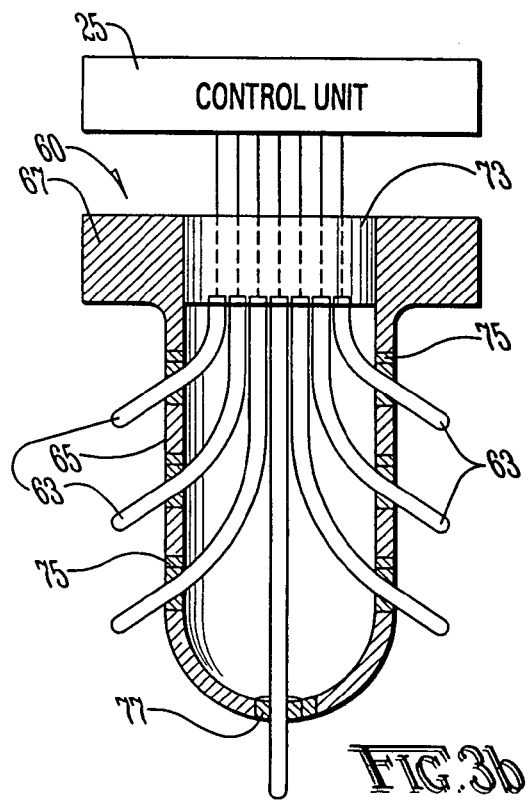
FIG. 3b is another depiction of a modified embodiment of the multi-purpose device for sensing and control of changes in brain state similar to FIG. 3a but showing the retractable elements in an extended configuration.

FIGS. 3a–3b depict a modified embodiment 60 of the present invention wherein extendable elements 63 can be extended into the surrounding tissue after a shaft portion 65 of the device 60 is implanted into a desired target region or tissue. The device structure 60 of this embodiment includes a base portion 67. The shaft portion 65 is first inserted into the target tissue after which the extendable elements 63 can be selectively extended into the surrounding tissue to thereby increase the contact area between the extendable elements 63 and the tissue, wherein the extendable elements 63 are extended either manually or by using tiny motors or other mechanical, magnetic or electromechanical means. Each of the extendable elements 63 used for cooling therapy, sometimes referred to herein as a cooling element 63, is hollow and made of biocompatible materials with high thermal conductivity such as gold, platinum, or other suitable thermally conductive material and may include a dividing wall, see inset of FIG. 3a, that allows coolant to be circulated from a proximal end thereof to a distal end thereof along one side of the extendable element 63 and to be circulated from the distal end thereof to the proximal end thereof along the other side of the extendable element 63. The extendable elements 63 used for cooling therapy are automatically filled with coolant in response to sensing of brain state changes as signaled by sensors to control apparatus. Upper ends of the extendable elements 63 used for cooling therapy have valves controlled by control apparatus for controlling the flow of coolant or refrigerant through the device 60. Coolant is pumped into the cooling elements 63 by a micro-pump located at an upper end 67. The ratio of the diameter of the protruding tubes to the diameter of the shaft may be larger than that depicted in FIG. 3, to allow implantation of more probes/unit volume, to thereby increase the rate of cooling without causing more tissue damage. This probe may be used to sense and control in one-, two-, or three-dimensions, depending on the orientation of the protruding tubes in reference to the shaft. The base 67 of the device can also be used for cooling the cortical surface. Coolant can also be put into the shaft as shown in FIG. 2a, 2b to enable the use of the shaft also for cooling.

The present invention enables successful control of brain state changes, such as prevention or blockage, or successful observance of safety constraints in response to sensor signals provided to the control apparatus that causes the control apparatus to automatically initiate and automatically terminate coolant flow through cooling elements 63 and to also pump any residual coolant from the shaft portion 65 back into reservoir 43. In an application of the present invention, see FIG. 3b, electrical, temperature and other sensors 75 are located in the shaft portion 65 of the device 60. The shaft portion 65 includes insulating portions 77 for separating cooling surfaces 63 from electrical contacts 75, and sensors 75 from each other. As before, the insulating portions 77 are constructed of materials such as polyurethane, Teflon or other suitable materials, such as Tecoflex™ or Silastic™, that preserve flexibility of the shaft portion 65. Those skilled in the art can appreciate that location and extent of the insulating portions 77 and cooling surfaces 63 can be varied as required by an application thereof.

In some applications of the present invention, selected ones of the extendable elements 63 may also act as electrical sensors, see FIG. 3c. Other sensors 83 for temperature, chemical, and other signals may also be disposed in the shaft portion 65, although such sensors may also be positioned on the extendable elements 63. Coolant or refrigerant is prevented from leaking into the surrounding tissue by using medical, biocompatible seals 81, such as seals presently available for such purposes. The cooling or sensor elements 63 protruding from the shaft portion 65 enable three-dimensional recording and control/therapy of brain state-changes, which provides greater range/scope, precision and flexibility for improved efficacy and safety, features not provided by prior art devices. All sensors 75, 83 are connected in communication with auxiliary systems such as signal recording/processing and analysis/decision/control systems via conductors 85 connected to control unit 25. Those skilled in the art can appreciate that signal transmission between sensors 75, 83 and control unit 25 to the auxiliary systems may be wireless. In that event, the device 60 would include a miniaturized transmitter mounted on an outer surface thereof.

The electrical sensors of the devices of the present invention are used to detect changes in brain activity, which sensors signal the control system 25 to initiate, and subsequently to terminate, the cooling therapy process, whether cooling or some other modality. It is to be understood that the signals from the sensors may arise from temperature, chemical or other physiological/biological phenomena that can be used to detect brain state changes. As the valves are automatically opened, the pressure differential causes the refrigerant to flow into the shaft and cool the cooling elements 63; in the case of coolants, a micropump 107, see FIG. 5a, is used to circulate the said to be pumped coolant through into the cooling elements 63. Once the safety limit is reached or the abnormal/undesirable activity has subsided, or the task of testing and mapping cortical functions has been completed, a micropump 107, see FIG. 5a, withdraws the refrigerant or coolant back into reservoir 43 to terminate the therapeutic intervention. Depending on the application, the device 60 or another device as disclosed herein, may be configured to sense and cool in one-, two- or three-dimensions by deploying into or retracting from the tissue, extendible elements in the x-, y-, and z-planes. Additionally, the shaft portion itself may comprise cooling surfaces to enhance and speed-up the cooling effect. In FIG. 4a, device 10, 60, or 150, as described herein, implanted into the brain is connected to control unit 25 placed under the skin, such as in the chest area, through conductors 97 (23, 85, or 177 in other designs), or in some applications wirelessly via telemetry, and coolant or refrigerant flows through tubes 99 to reservoir 43 also placed in the chest area. The control units 25 generally comprise a processor or a microprocessor or a digital signal processor, memory for storing instructions, and a battery. The reservoir 43 may include tanks for coolant or pressurized cans for refrigerant. It is to be understood that the control units 25 and reservoir 43 may be placed at any convenient and accessible location on the body. For example, the control units can be placed in or on the skull as disclosed in U.S. Pat. No. 6,560,486 of Ivan Osorio, issued May 6, 2003, or outside the body/skin. FIG. 4a depicts one of several possible locations of the control/storage units and FIG. 4b depicts a schematic representation of the operation of the device. Details of operation of the mechanical components are indicated in FIGS. 5a and 5b. For purposes of clarity, many of the Figures do not show the electrical conductors or sensors. The base of the device 11 includes micropumps 107 and microactuators 109 to pump and control the flow of the coolant or refrigerant into the shaft portion 113. The flow of the coolant or the refrigerant is controlled by valves 115. In an embodiment having extendable tubes, screws 117 are connected to the top of the extendable tubes via a plate 123, which can be used to push the extendible tubes device into the target tissue, once the shaft portion is positioned within the tissue. The screws 117 can be operated manually or automatically by using motors connected to the control units 25. The flexible but less deformable or more rigid, compared to stiff tubes in other embodiments disclosed herein, inner tubes 125 are directed into the tissue by guides 127 attached to the shaft portion. Those having skill in the art can appreciate that mandrels can also be used to push the extendable tubes into the target tissue and then withdrawn, leaving the tubes outside the main shaft and in contact with the target tissue; the mandrels or extendible tubes or elements may be made of materials that are malleable or are "intelligent," such as memory metal alloy (e.g. biocompatible nickel-titanium shape memory metal alloy), which remembers its original pre-determined shape. The tubes containing coolant or refrigerant are sealed using medical, biocompatible seals 133 to prevent leakage of coolant or refrigerant into the surrounding tissue. Cooling through the extendable tubes can be accomplished by either a coolant or a refrigerant. In case of a coolant, the pump 107 circulates the coolant through the extendible tubes, which have a dividing wall for the return path of the coolant, similar to that shown in the inset in FIG. 3a (FIG. 3d). Although only one design is shown for the return path of the coolant, other designs may be used to allow a continuous flow of the coolant. If a refrigerant is used to apply cooling therapy to the target tissue, an appropriate valve 115 is opened through the use of actuators 109 and the chilled refrigerant expands into the shaft portion of the device and the extendable tubes thereby cooling the tubes; a wall dividing the extendible tubes may not be required in this case. The extendible tubes in this case can be simply hollow as there is no free circulation of the refrigerant. To terminate cooling, the actuators are used to close the previously opened valve and open another valve to thereby enable a pump to withdraw the coolant or the refrigerant from the shaft portion. The pressure and temperature in the tubes are controlled by the control units 25.

For an application using refrigerant instead of coolant, any low pressure and non-flammable refrigerant may be used, such as those commonly used for pressurized air cleaners, i.e., tetrafluoroethane. The refrigerant is maintained at an elevated pressure in a storage unit 43, a microactuator 109 opens the valve 115 allowing the pressure differential of the refrigerant to cause the refrigerant to flow into the shaft portion or the extendible tubes as determined by the particular embodiment being used for the application to thereby rapidly cool the target tissue. Those familiar with the art appreciate that a valve may also open or close automatically due to the flow direction or pressure gradients, without actually needing an actuator to control it. In addition, the used refrigerant may be vented out into the air or it may be stored in a container adjacent to the reservoir 43. When cooling therapy needs to be terminated, a pump 107 withdraws the refrigerant from the tubes after a valve is opened that facilitates flow of the refrigerant in the appropriate direction. Existing miniature or micro-actuators using various technologies, including but not limited to piezoelectric, capacitive, electrochemical or magnetic actuators, may be used for this purpose. Similarly, existing pumps that are small enough to fit in the device structure and with appropriate flow rate in the range of approximately 1 microliter/sec to 1 milliliter/sec, may be used.

It is to be understood that for some applications, the extendable cooling elements hereinbefore described may be replaced with solid highly thermally conductive elements. In that event, the coolant or refrigerant resides in the shaft portion or at the base of the device and is spaced apart from the material exposed to the tissue, thereby obviating the need to use seals. Cooling is achieved by passive conduction through the solid, highly thermally conductive tubes. In this mode, the protruding elements are exposed to the coolant, refrigerant or other suitable media at the top of the device or in the shaft and cooling is passively transferred to the target tissue through the high thermal conductivity of the elements or the shaft portion. Materials of high thermal conductivity that can be used include, but are not limited to, carbon nanotubes, ceramics and other carbon or silicon composites. If a coolant is used, it can be recirculated indefinitely, provided its thermo-physical properties remain unchanged and it does not become contaminated. For refrigerants, replacement is obviously required before the contents of pressurized containers become depleted. The control units may have sensors to check the physical characteristics of the coolant and refrigerant supply such as pressure, temperature, etc., and may be programmed to alert the user as to the status of those characteristics.

Figure 6A:
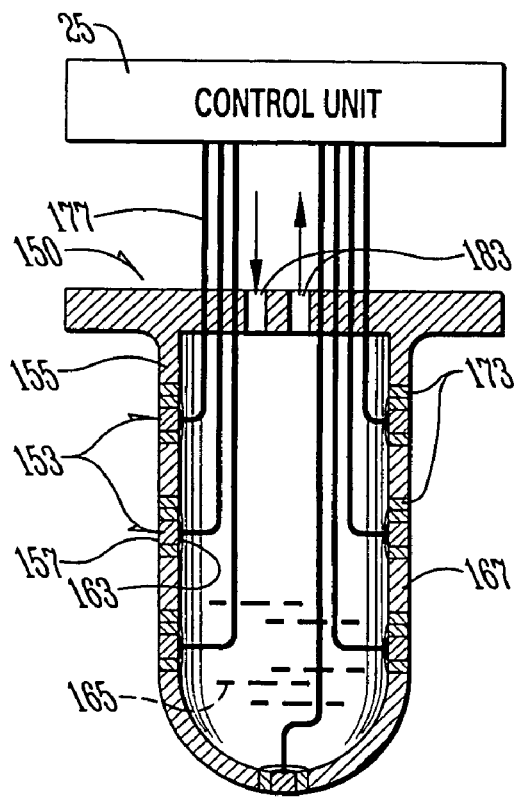
FIGS. 6a and 6b depict a modified embodiment of the multi-purpose device for sensing and control of changes in brain state, using thermoelectric devices for applying cooling therapy, according to the present invention.
Figure 6B:
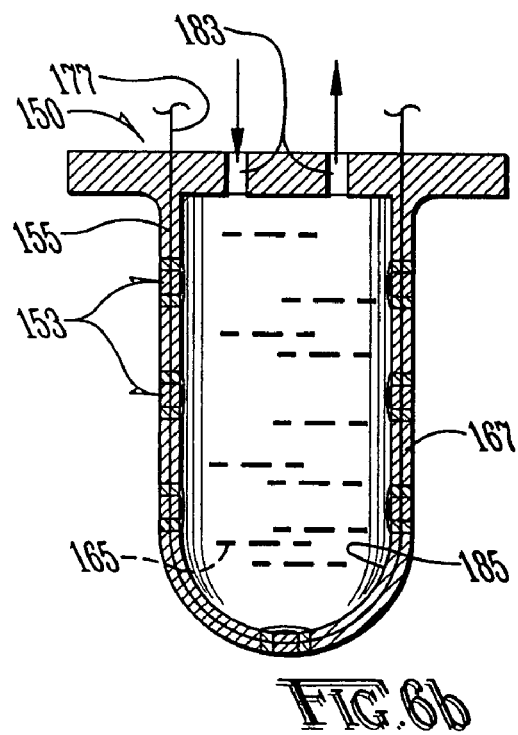

Another modified embodiment 150 of the device of the present invention is depicted in FIGS. 6a and 6b wherein cooling therapy is administered by using thermoelectric (TE) devices 153. The flow of coolant in these embodiments is similar to the ones in FIG. 2. In this embodiment 150, the TE devices 153 are placed in the shaft portion 155 whereat the cooled side surfaces 157 of the devices 153 are exposed to target tissue while the warmed surfaces 163 of the devices are inside the shaft portion, away from the tissue and facing the coolant or refrigerant 165 flowing therethrough. The TE devices 153 in the shaft portion 155 are separated from each other by insulation 167 as hereinbefore disclosed. Other electrical, thermal, chemical or physical sensors 173 can be placed in the shaft portion 155 of the device 150 for recording relevant signals as disclosed herein. Those skilled in the art can appreciate that the location of these sensors 173 in relation to the TE devices 153 or any other cooling elements, may vary depending on the application and the type of signals being monitored or recorded. The sensors 173 are connected to control units 25 via conductors 177; for some applications, communication between sensors 173 and control units 25 may be wireless if appropriate. Openings 183 provide access for coolant or refrigerant flowing into the shaft portion 155. As with other embodiments disclosed herein, seals are used to prevent the leakage of coolant or refrigerant into the surrounding target tissue. The shaft/device of the present invention as depicted in FIG. 6b does not require seals as there are no openings into the target tissue; thus, coolant or refrigerant can flow freely within inner wall 185 and thereby be in thermal contact with the warmed surfaces 163 of the TE devices 153. The extent of the insulation may be varied according to the application.

Figure 7A:
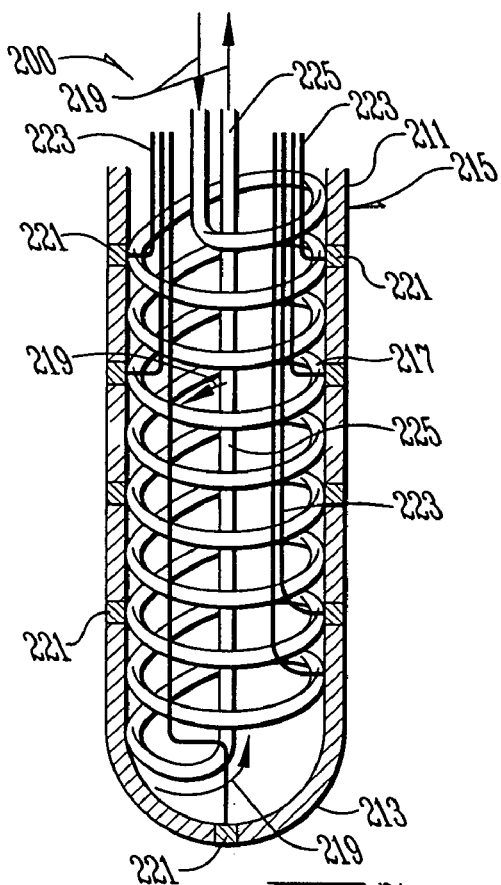
FIG. 7a depicts another modified embodiment of the multi-purpose device for sensing and control of changes in brain state, wherein a coolant-carrying conduit in a shaft portion thereof has a spiral configuration and wherein a return conduit for the coolant is centrally positioned in the spiral, according to the present invention.
Figure 7B:
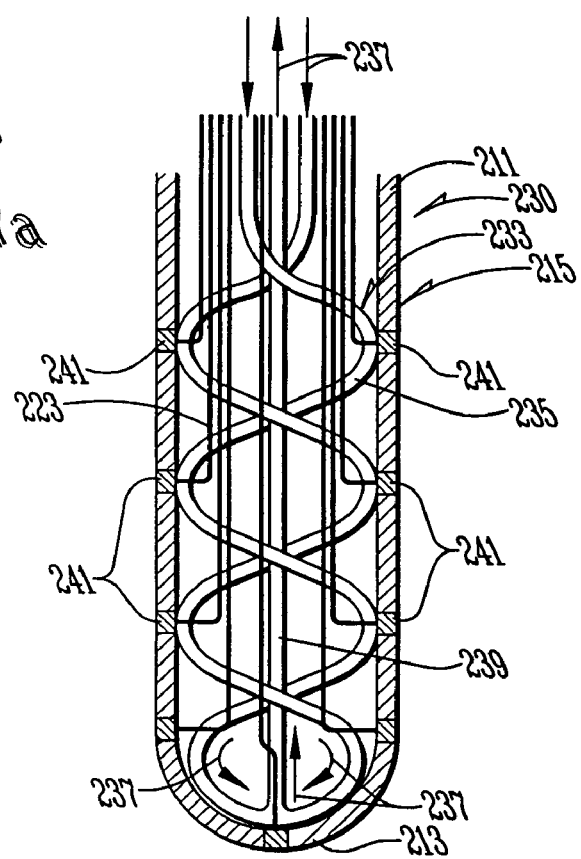
FIG. 7b depicts a variation of the embodiment depicted in FIG. 7a, wherein two coolant-carrying conduits in the shaft portion have a double helix configuration and wherein a centrally positioned return conduit provides a return path for coolant carried by the two double helix conduits, according to the present invention.
Figure 7C:
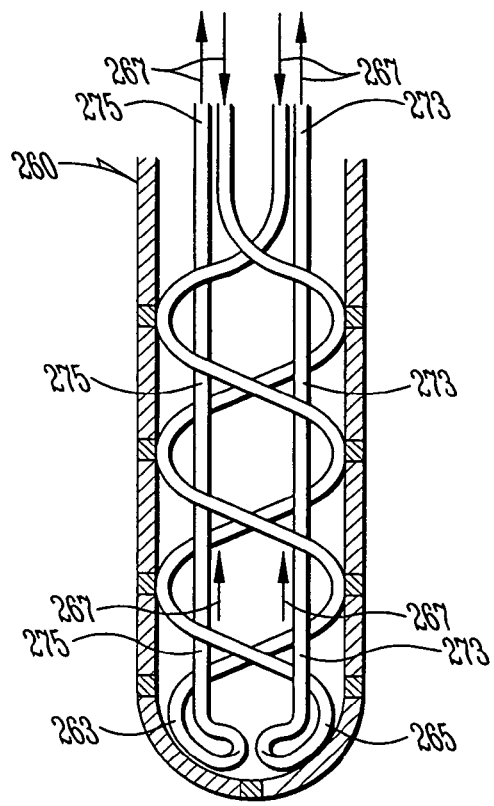
FIG. 7c depicts another variation of the embodiment depicted in FIG. 7a, wherein two coolant-carrying conduits in the shaft portion have a double helix configuration and wherein a separate return conduit provides a return path for the coolant carried by each helix conduit, according to the present invention.

Another modified embodiment 200 of the multi-purpose device of the present invention for simultaneous sensing and control of changes in brain state and cooling of brain tissue is depicted in FIGS. 7a through 7c. Many of the features of the modified device are substantially similar to those hereinbefore described. As a result, repetitive descriptions thereof will not be reiterated here in detail.

Device 200 comprises a proximal end 211 and a distal end 213, wherein the proximal end 211 is operatively positioned closer to the skull than the distal end 213. The proximal end 211 and the distal end 213 are housed in a shaft portion 215. Device 200 includes at least one spiral hollow tube or conduit 217 for carrying a coolant or a refrigerant 219 from a reservoir (not shown) located external to the device 200 into the conduit 217. The conduit 217 has a helix or spiral configuration which operatively increases the surface area thereof to thereby maximize heat transfer between the device 200 and the adjoining brain tissue. Various sensors 221 are positioned on shaft portion 215 for receiving electrical and other chemical or physical signals from the brain tissue with conductors 223 carrying those signals to control units (not shown) located outside the device 200. A centrally located conduit 225 provides a return path to the external reservoir for the coolant or refrigerant 219 flowing through the spiral conduit 217. The spiral configuration of the internal cooling tube 217 maximizes the area of contact between the coolant 219 and the shaft portion 215 and consequently the brain tissue, thus enabling rapid cooling of the brain tissue.

A variation 230 of embodiment 200 is depicted in FIG. 7*b*, wherein device 230 includes two conduits 233 and 235 intertwined in a double helix configuration through which coolant or the refrigerant 237 circulates from a reservoir located external to device 230. A centrally located return conduit 239 provides a return path to the external reservoir for the coolant or refrigerant 237 flowing through both of the spiral conduits 233, 235. The spiralling of the two conduits 233, 235 may be more tightly wound than that shown to thereby maximize the heat transfer between the device 230 and the brain tissue. Sensors 241 relay tissue signals to processing/control units (not shown) which can be used to initiate and/or terminate cooling of selected brain tissue by controlling the flow of coolant or refrigerant 237 through conduits 233, 235. By so doing, both safety and efficacy of the cooling therapy can be monitored via sensors 241.

Another variation 260 of embodiment 200 is depicted in FIG. 7*c*, wherein device 260 includes two spiral conduits 263 and 265 intertwined in a double helix configuration through which coolant or refrigerant 267 circulates from a reservoir located outside device 260 wherein two separate return conduits 273, 275 positioned within the spiral conduits 263, 265 provide separate return paths to the external reservoir for the coolant or refrigerant 267 carried by the spiral conduits 263, 265. The sensors and conductors connected thereto are not shown in FIG. 7(*c*) for purposes of clarity and can be placed anywhere on the outer wall of the shaft. The return paths for the coolant through tubes 275 may be positioned anywhere in the main shaft, although it is shown to be at the center.

Figure 8:
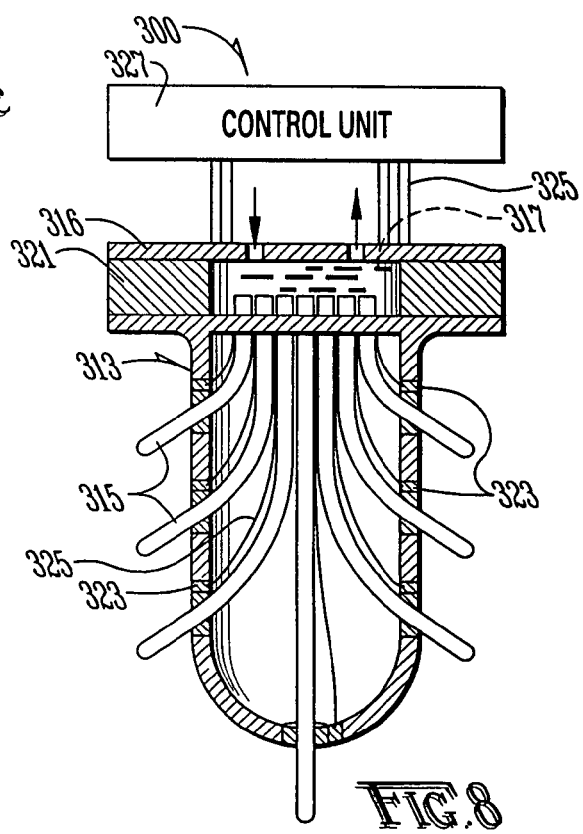
FIG. 8 depicts yet another modified embodiment of the multi-purpose device for sensing and control of changes in brain state, wherein a shaft portion thereof includes multiple deployable hollow tubes, according to the present invention.
Figure 9A:
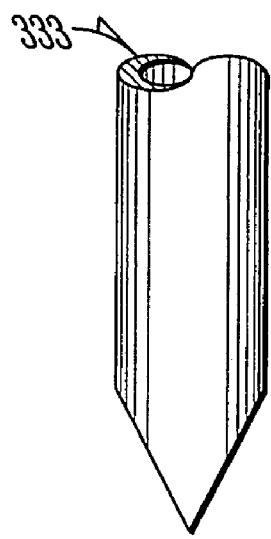
FIG. 9a, 9b depict various exemplary conductive tips for the multi-purpose device for sensing and control of changes in brain state, according to the present invention.
Figure 9B:
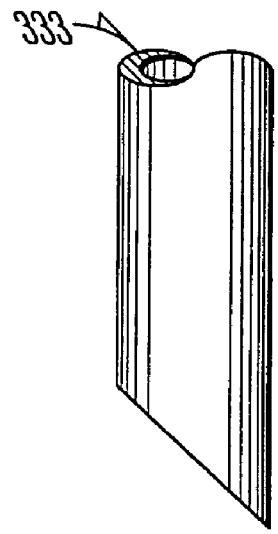
Figure 9C:
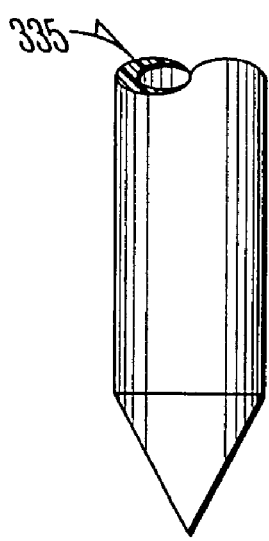
FIG. 9c, 9d depict various exemplary tips for the multi-purpose device for sensing and control of changes in brain state wherein a conductive portion thereof protrudes beyond an insulative sleeve or coating, according to the present invention.
Figure 9D:
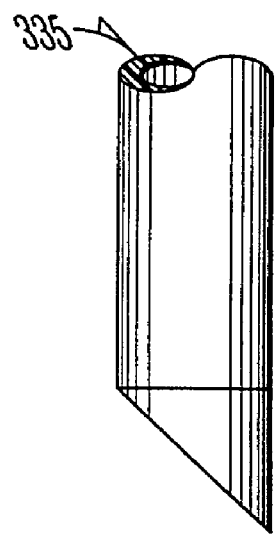

Yet another modified embodiment 300 of the multipurpose device of the present invention for simultaneous sensing and control of changes in brain state and cooling of brain tissue is depicted in FIGS. 8, 9*a* and 9*c*. Many of the features of device 300 are substantially similar to those hereinbefore described, particularly in regard to embodiment 60; therefore, the descriptions thereof will not be reiterated herein in detail.

Device 300 includes a shaft portion 313 with extendible hollow tubes 315 constructed of a biocompatible pliable material. As the shaft portion 313 is inserted into brain tissue, the hollow tubes 315 are retained inside the shaft portion 313, but once the shaft portion 313 has reached its target, pressurizing means 316, such as micropumps or other suitable means, are used to pressurize the hollow tubes 315 with fluid 317 to a pressure sufficient to enhance the rigidity of the tubes 315 to thereby overcome tissue elasticity and to simultaneously advance the tubes into the brain tissue surrounding the shaft portion 313. After the tubes 315 are fully deployed, the fluid 317 may be withdrawn from the tubes 315. Alternatively, the proximal ends of the pliable hollow tubes 315 may be embedded in a rigid ring-like mechanism 321 through which force may be applied to advance the fluid-filled tubes 315 either manually or by using one or more stepper motors as hereinbefore described. Again, sensors 323 on the hollow tubes 315 and/or on an outer perimeter of the shaft portion 313 and conductors 325 connected to the sensors 323 carry brain signals to control units 327 located outside the device 300. Those skilled in the art can appreciate that the hollow tubes 315 may be also inserted into brain tissue via mandrels or other suitable means and that the biocompatible material, of which the tubes 315 are constructed, may be rigid.

Exemplary tip configurations 333, 335 for distal ends of the tubes 315 are depicted in FIGS. 9*a* and 9*b*. The tips on the tubes 315 are variously configured to facilitate insertion of the tubes 315 into brain tissue and to minimize injury. The tips may be constructed of thermally or electrically conductive or non-conductive materials depending on the application.

Figure 10A:
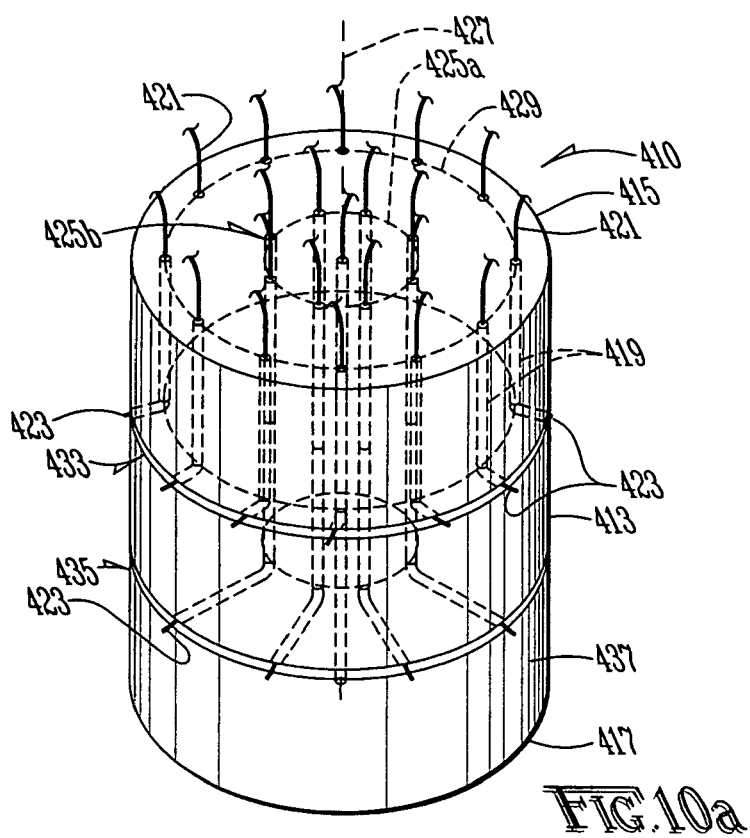
FIG. 10A depicts another embodiment of the unitized device with three-dimensional capabilities for sensing and control of brain state changes showing a main shaft thereof having clusters of hollow conduits or tubes with wires or elements positioned therein such that the wires or elements can be displaced to extend outwardly from an outer surface of the main shaft.
Figure 10B:
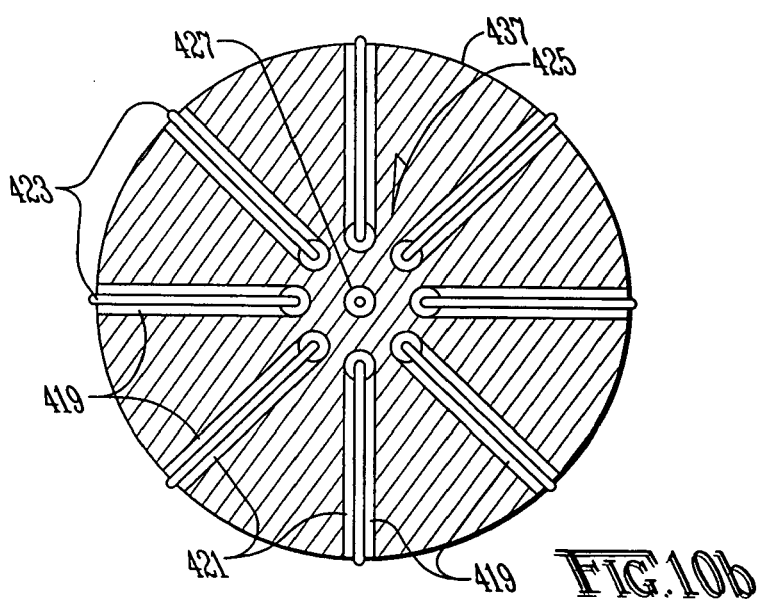
FIG. 10B depicts a cross-sectional view of the device depicted in FIG. 10a illustrating the wires or elements having been displaced to extend outwardly from the outer surface of the main shaft.

Other modified embodiments of the unitized device with three-dimensional capabilities for sensing and control of brain state changes are depicted in FIGS. 10A through 10C. Embodiment 410, shown in FIGS. 10A–10C and 11 and similar to the embodiment shown in FIGS. 3 and 8, comprises a main solid shaft 413 having a proximal end 415 that is generally operatively positioned closer to the skull than a distal end 417 thereof. A plurality of hollow tubes or conduits 419 are positioned internally within the main shaft 413 to provide fixed paths for guided deployment of elements such as tubes (for carrying the coolant or the refrigerant) or wires 421 for multi-dimensional acquisition of signals (electrical, physical, chemical, etc.) as hereinbefore described via contacts/sensors 423 at the tips or anywhere along the exposed elements 421. These hollow tubes or conduits are made by boring holes into the shaft and these conduits open out of the shaft at different distances 433 and 435 from the proximal end of the shaft. It is to be understood that the wires or tubes 421 are connected to various external devices (not shown) as hereinbefore described.

The hollow conduits 419 are arranged in concentric clusters 425, each cluster 425 generally being positioned at a different radial distance from a centrally located axis 427 of main shaft 413. Generally, and to facilitate deployment of elements 421, a cluster 425*a* of conduits 419, spaced farther from axis 427 may be made to have lengths that are shorter than conduits 419 of cluster 425*b* spaced closer to axis 427 with the shorter conduits 419 of cluster 425*a* exiting at a level 435 that is closer to the proximal end 415 of main shaft 413 than a level 433 at which the longer conduits 419 of cluster 425*b* exit. As a result of this concentric, multi-level arrangement of the clusters 425 of conduits 419, more efficient use of the limited available spacing is obtained, which facilitates enhanced flexibility of spatial coverage of signal acquisition in single- or multi-dimensional arrangements. The length, diameter, and number of conduits that may be used in electrodea device structure of the present invention may vary with application. It is to be understood that the device of the present invention for a particular application may have only one level or may have several levels as described herein. Those skilled in the art appreciate that the shaft itself may be cooled with coolant or refrigerants so as to enhance heat transfer or used for signal (physical or chemical) acquisition FIG. 10B depicts a schematic cross-sectional view of electrodea device, similar to that shown in FIG. 10A, illustrating an example of a cluster 425 of conduits 419, spaced around axis 427 and arranged to operatively guide the tubes or wires 421 with contacts 423 into the surrounding tissue. At each level 433, 435, the conduits 419 internally approach outer surface 437 of the main shaft 413 such that wires 421 or contacts 423 extended therethrough are directed outwardly, either perpendicularly or at other angles, relative to the outer surface 437 of the main shaft 413, as desired with respect to a particular application and the geometry of the target tissue of that application. FIG. 10C depicts a manner in which the conduits 419 may be structured in order to direct a tube or wire 421 with contact 423 extended therethrough in a particular direction. For some applications, tubes 419 parallel to axis 427 of the main shaft 413 may also protrude through an opening 441 in distal end 417, as shown in FIG. 10C.

FIG. 11 depicts an embodiment 450 of the present invention wherein clusters 453 of conduits, such as clusters 455 and 457, are arranged in patterns that are non-concentric relative to each other or to a central axis 459 of a main shaft 461. It is to be understood that a device of the present invention may include conduits spaced without clustering and may also include one or more clusters of conduits, one or more of which may be arranged concentrically and/or one or more of which may be arranged non-concentrically as herein described.

In an application, the main shaft of the device is first inserted into tissue with the tubes or contacts not extending beyond the outer surface of the main shaft as in FIGS. 3 and 8. Once the main shaft is suitably in place relative to the target tissue, the tubes and contacts are extended through the conduits into the target tissue. The elasticity of the tissue holds the shaft in place for the wires or tubes to be extended into the tissue. If necessary, mandrels (not shown) may be used to assist with extending the wires and contacts into the tissue; however, for some applications, the tubes and contacts may be constructed of material with sufficient stiffness relative to the resilience of the target tissue that the use of mandrels may not be necessary. The tubes for carrying the coolant or the refrigerant are designed as shown in the inlet of FIG. 3a. The means for pumping the coolant or the refrigerant also remain the same as disclosed earlier in this application and will not be repeated here.

It is to be understood that the conduits may be structured and configured for various other applications, such as electrical stimulation therapy or drug delivery.

Figure 12A:
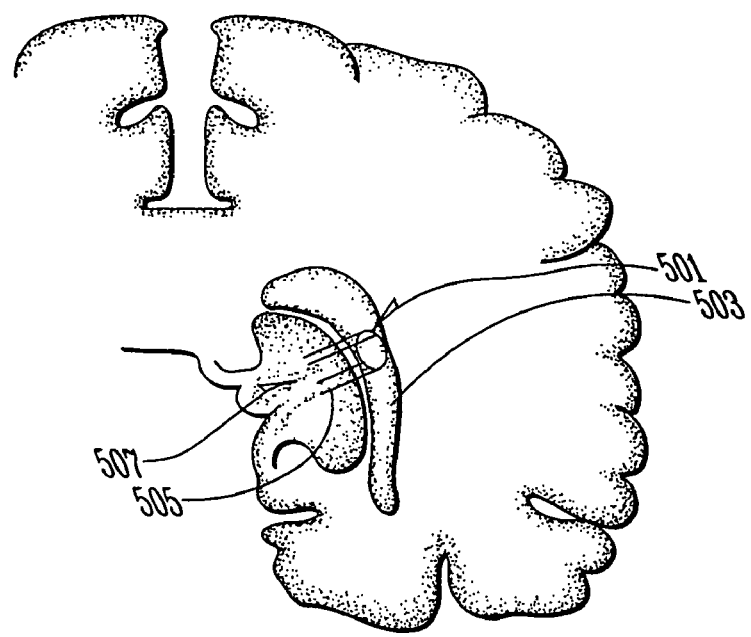
FIGS. 12a and 12b depict an application of the disclosed device where the shaft is inserted into the ventricle and the extendible elements are then pushed into the adjacent tissue (such as hippocampus).
Figure 12B:
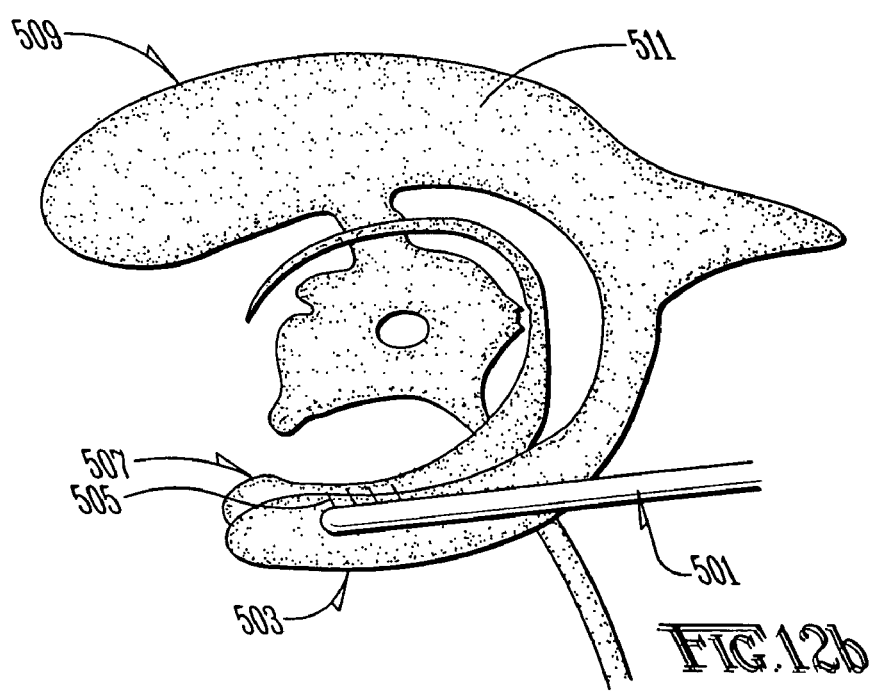

FIG. 12a depicts a method of using the device in FIG. 3 where the shaft of the device is inserted into a ventricle and the extendible tubes 505 are pushed into the adjacent tissue. For example, in FIG. 12, the shaft 501 is placed in the temporal horn of the lateral ventricle 503 and the extendible tubes 505 are extended on the mesial side into the amygdala and the hippocampus 507. FIG. 12b shows a lateral view of the approach for clarity with the lateral ventricle 509 filled with the cerebrospinal fluid 511. This method enables precooling of the ventricle to a temperature that does not affect its function and then using the extendible tubes to rapidly cool the hippocampus when the sensors detect a state change.

Figure 13:
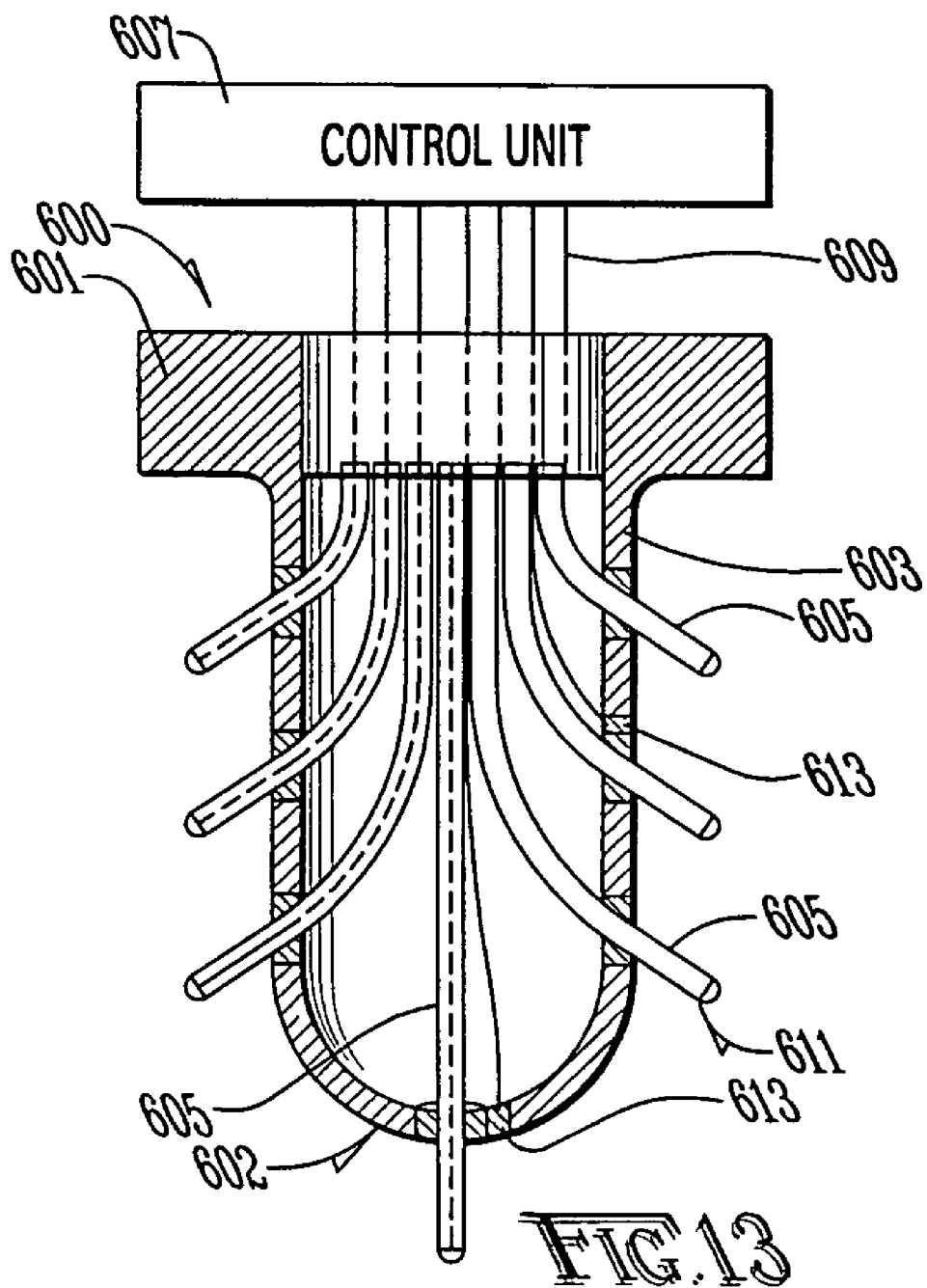
FIG. 13 shows a design where the device can be used to deliver drugs into the brain tissue.

Another embodiment of the present invention depicted in FIG. 13, which is similar to FIG. 3, can be used to deliver drugs or chemicals for the treatment of seizures or other neurological disorders that can stop seizures or other disorders very close to the target area. Most of the characteristics of the invention depicted in FIG. 13 are similar to the embodiment depicted in FIG. 3. Instead of coolant or refrigerant, the conduits/tubes carry a drug of interest into the shaft and the extendible tubes. The tips of the extendible tubes have valves that can be selectively controlled and opened by the control units so that the drug can be released contingent on a specific event, similar to that of the cooling therapy. The drug delivery can also be terminated, as with the cooling therapy, whenever a safety constraint is reached or when event is terminated. The embodiment of the present invention as depicted in FIG. 13 can be described as follows. The embodiment consists of an electrode structure 600 with a proximal end 601 that is spaced closer to the skull than distal end 602, which is positioned in the brain tissue. The electrode structure includes a shaft 603 that is first placed in the target area and consists of thin extendable tubes 605 that can be pushed into the tissue after the shaft 603 is placed in the tissue. The extendible tubes and the shaft can reach deeper regions of the cortex and, further, can be used to deliver the drug into a diffuse area in order to overcome diffusivity problems of the brain tissue. The mechanical or other means used for pushing these extendable tubes 605 into the tissue are similar to those of the embodiment depicted in FIG. 3. The extendable tubes have valves 611 at the tips that can be controlled by the control unit 607 (not inside the brain) via wires 609. These wires also connect to other sensors that can be used to measure physical, chemical, or electrical signals through sensors 613 placed in the shaft or at the tips of the extendable tubes 605. The drug carried by the tubes can be released into the tissue on cue from any of the signals being recorded by the control unit. The drug release can also be terminated by use of information from the same signals. Those skilled in that art will appreciate that with appropriate modifications, the electrodes disclosed for the present invention may be multi-purpose: cooling and delivery of chemical and electrical therapies may performed by means of the same electrode. Although only the structure in FIG. 13 is described for use in drug delivery, any of the structures disclosed herein can be used for drug delivery with minor and appropriate modifications. It is to be understood that the disclosure herein is just an example of how drug delivery can be accomplished using the embodiments of the present invention disclosed herein and should not be considered as being limited to only the particular electrode structures described.

Another embodiment of the present invention depicted in FIG. 13 can be used to deliver drugs or chemicals for control of state changes, such as seizures or other neurological disorders, very close to the area of interest. Most of the characteristics of the invention depicted in FIG. 13 are similar to the embodiment depicted in FIG. 3. Instead of coolant or refrigerant, the conduits/tubes carry the drug of interest into the shaft and the extendable tubes. The tips of the extendable tubes have valves that can be selectively controlled and opened by the control units so that the drug can be released contingent on a specific event, similar to the cooling therapy. The drug delivery can also be terminated as with the cooling therapy whenever a safety constraint is reached or when event is terminated. This embodiment of the invention as depicted in FIG. 13 can be described as follows. The embodiment consists of a device structure 600 with a proximal end 601 that is spaced closer to the skull than the distal end 602, which is positioned in the brain tissue. The device structure has a shaft 603 that is first placed in the target area and consists of thin extendable tubes 605 that can be pushed into the tissue after the shaft 603 is placed in the tissue. The extendable tubes and the shaft allow chemicals to reach parts of cortex, white matter and deep nuclei within seconds, as opposed to minutes if the chemicals had been delivered to the cortical surface The mechanical or other means used for pushing these extendable tubes 605 into the tissue are similar to those of the embodiment depicted in FIG. 3. The extendable tubes have valves 611 at the tips that can be controlled by the control unit 607 (not inside the brain) via wires 609. These wires also connect to other sensors that can be used to measure physical, chemical, or electrical signals through sensors 613 placed in the shaft or at the tips of the extendable tubes 605. Means for pumping the chemicals such as a micro-pump were not depicted in FIG. 13 but may be used depending on the application. The pumps and valves in this embodiment operate similar to the embodiment depicted in FIG. 3. Because the drug/chemical is released into the tissue, a return path for the coolant is not needed for this embodiment. The drug carried by the tubes can be released into the tissue on cue from any of the signals being recorded by the control unit. The drug release can also be terminated by using information from the same signals. Diffusion of chemicals into brain tissue may be passive or it may be enhanced by safely pressurizing the chemicals or by using ultrasound or by using both. Those skilled in the art would appreciate that with appropriate modifications, the devices disclosed herein are multi-purpose: cooling and delivery of chemicals and of electricity may be performed through the same device. As an example, in one of several possible embodiments for multimodal control, the chemical delivered into the tissue may be used also as a coolant by lowering its temperature to a safe and efficacious level. Although only the structure depicted in FIG. 13 is specifically described for use in drug delivery, any of the other devices or structures disclosed herein can be used for drug delivery with minor and appropriate modifications. The disclosed invention is just an example of how drug delivery can be accomplished using the inventions disclosed in this application and should not be considered as limited to any particular device structure.

Delivery of chemical compounds and electrical stimulation both are known to be useful in controlling certain brain states and/or changes between states. However, their usefulness can be enhanced by relating the time(s) at which they are delivered to the time(s) at which temperature regulation therapy is applied. Multimodal control (cooling+electrical stimulation, cooling+chemical delivery, or cooling+electrical stimulation+chemical delivery) of brain state changes can be exerted through an embodiment disclosed herein; any or all of the control modalities in any combination may be delivered in any temporal sequence, including simultaneously, using the a single device. The multimodal approach provides a generalization of any prior single-modality therapy, thereby offering improved efficacy, tolerability and safety than unimodal (i.e., electrical stimulation). This may be due in part to a potential synergism among these modalities, so that the decrease in temperature, current densities and amounts of chemicals required to block or abort a change of state, may be lower when delivered in combination than when delivered singly. Delivery of chemical compounds using the devices disclosed herein, may be through openings or perforations in the main shaft and/or extendible elements and may require that the device has as many compartments as there are control modalities. For example, in the case of a device for cooling and delivery of chemical compounds, each will flow through separate compartments hermetically sealed to avoid contamination. The pores or holes in the main shaft or extendible elements may be continuously open or may have micro- or nano-valves whose opening and closing will be controlled by an actuator mechanism or other mechanism with similar functional capabilities. Control modalities may share extendible elements or may be delivered through separate elements.

The various embodiments disclosed herein enable accessing of physical, chemical, and electrical signals from brain tissue simultaneously with cooling of the brain tissue.

Those skilled in the art can appreciate that while cooling is the preferred method for control of state changes, safe increases in tissue temperature may be induced to control brain state changes, via the devices disclosed herein. By enhancing inherent noise through augmented Brownian motion of ions and vibrations of membrane proteins especially of those associated with ion channels or exocytotic sites, temperature elevations may "scramble" signal transmission between neurons or structures. Although the disclosure herein describes the use of coolants, those familiar with the art appreciate that tissue temperature can also be elevated within safe limits using liquids or other means to control brain tissue state changes.

It is to be understood that while certain forms of the present invention have been illustrated and described herein, it is not to be limited to the specific forms or arrangement of parts described and shown.

What is claimed and desired to be secured by Letters Patent is as follows:

1. A device for control of tissue temperature in three dimensions, comprising;
    (a) a shaft portion having a distal end, wherein the shaft portion is structured for insertion into target tissue of a subject patient;
    (b) cooling means structured to change temperature within the target tissue, wherein the cooling means includes:
        (1) at least one cluster of conduits spaced inside the shaft portion and extending out of the shaft portion at a first distance from a surface of the tissue, wherein each conduit of the at least one cluster of conduits is structured to carry extendable wires or tubes into the target tissue;
        (2) advancing means structured to selectively advance the at least one extendable wires or tubes through the conduits of the at least one cluster of conduits into brain tissue surrounding the shaft portion.

2. The device as described in claim 1, wherein the at least one cluster of conduits includes a plurality of clusters of conduits to facilitate insertion of wires or tubes into the tissue surrounding the shaft portion.

3. The device as described in claim 1, wherein at least one cluster of conduits open into the tissue surrounding the shaft portion at a second distance from a surface of the tissue, wherein the second distance is different from the first distance.

4. The device as described in claim 1, wherein the conduits of the at least one cluster of conduits open into the surrounding tissue at any desirable angle with respect to the axis of the shaft portion.

5. The device as described in claim 1, wherein the control means is structured to provide cooling and electrical stimulation.

6. The device as described in claim 1, further configured to enable delivery of chemicals or drugs into tissue into different locations in three dimensions, further comprising;
    (a) pumping means configured to pump at least one desired drug or chemical, wherein the pumping means includes:
        (1) at least one extendable tube housed within the shaft portion and structured to be extended outwardly from the shaft portion, and
        (2) advancing means structured to advance the at least one extendable tube into brain tissue surrounding the shaft portion;

(b) control means structured to regulate the flow of the drug or chemical into or through the shaft and/or at least one extendable tube into the target tissue; and (c) an energy source for powering the various components of the device.

7. The device as described in claim 6, further comprising:

(a) sensing means including at least one sensor monitoring a biological signal of the subject patient; and (b) wherein the control means are configured to detect or predict a change in the biological signal that is indicative of the occurrence of a change of state and, in response thereto, to automatically deliver a prespecified amount of drug or chemical into the target tissue.

8. The device as described in claim 6, wherein, the drug or chemical can be cooled to a desired temperature and the temperature of the target tissue can be controlled.

9. The device as described in claim 6, wherein delivery of the drug or chemical occurs through a the distal end of the shaft portion.

10. A device for control of tissue temperature in three dimensions, comprising;

(a) a shaft portion structured for insertion into target tissue of a subject patient;

(b) an external reservoir containing coolant or refrigerant;

(c) cooling means configured to change temperature within the target tissue, wherein the cooling means includes:

(1) a least one inflow conduit structured to carry coolant or refrigerant from the reservoir to and through the shaft portion, the at least one inflow conduit having a spiral shape; and (2) at least one return conduit structured to carry coolant or refrigerant from the at least one inflow conduit to the reservoir;

(d) control means structured to control the flow of coolant or refrigerant through the at least one inflow and/or return conduits; and (e) an energy source for powering the various components of the device.

11. A device for control of tissue temperature in three dimensions, comprising;

(a) a shaft portion structured for insertion into target tissue of a subject patient;

(b) an external reservoir containing coolant or refrigerant;

(c) cooling means configured to change temperature within the target tissue, wherein the cooling means includes:

(1) a least one inflow conduit structured to carry coolant or refrigerant from the reservoir to and through the shaft portion, the at least one inflow conduit including two spiral conduits intertwined in a double helix configuration; and (2) at least one return conduit structured to carry coolant or refrigerant from the at least one inflow conduit to the reservoir, the at least one return conduit being located inside the two spiral conduits to provide a return path to the reservoir for the coolant or refrigerant carried by the two spiral conduits;

(d) control means structured to control the flow of coolant or refrigerant through the at least one inflow and/or return conduits; and (e) an energy source for powering the various components of the device.

12. A device for control of tissue temperature in three dimensions, comprising;

(a) a shaft portion structured for insertion into target tissue of a subject patient;

(b) an external reservoir containing coolant or refrigerant;

(c) cooling means configured to change temperature within the target tissue, wherein the cooling means includes:

(1) at least one inflow conduit structured to carry coolant or refrigerant from the reservoir to and through the shaft portion, the at least one inflow conduit including two spiral conduits having a double helix configuration; and (2) at least one return conduit structured to carry coolant or refrigerant from the at least one inflow conduit to the reservoir, the at least one return conduit including two separate return conduits positioned within the two spiral conduits to provide separate return paths to the reservoir for the coolant or refrigerant carried by the two spiral conduits;

(d) control means structured to control the flow of coolant or refrigerant through the at least one inflow and/or return conduits; and (e) an energy source for powering the various components of the device.

* * * * *